US012258539B2

United States Patent
Scheibel et al.

(10) Patent No.: US 12,258,539 B2
(45) Date of Patent: *Mar. 25, 2025

(54) METHODS FOR PRODUCING ALKYLBENZENES, PARAFFINS, OLEFINS AND OXO ALCOHOLS FROM WASTE PLASTIC FEEDSTOCKS

(71) Applicant: The Procter & Gamble Company, Cincinnati, OH (US)

(72) Inventors: Jeffrey John Scheibel, Glendale, OH (US); Phillip Kyle Vinson, Fairfield, OH (US); Scott Leroy Cron, Liberty Township, OH (US); Thomas Earl Williams, Jackson Township, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/080,872

(22) Filed: Oct. 27, 2020

(65) Prior Publication Data

US 2021/0108154 A1 Apr. 15, 2021

Related U.S. Application Data

(62) Division of application No. 16/385,040, filed on Apr. 16, 2019, now abandoned, which is a division of
(Continued)

(51) Int. Cl.
  *C11D 1/22* (2006.01)
  *C07B 41/02* (2006.01)
(Continued)

(52) U.S. Cl.
  CPC .............. *C11D 1/22* (2013.01); *C07B 41/02* (2013.01); *C07B 41/04* (2013.01); *C07B 45/04* (2013.01);
(Continued)

(58) Field of Classification Search
  None
  See application file for complete search history.

(56) References Cited

U.S. PATENT DOCUMENTS 6,015,781 A * 1/2000 Vinson .................... C11D 1/123
  510/276
6,093,856 A * 7/2000 Cripe ...................... C07C 43/11
  568/625
(Continued)

FOREIGN PATENT DOCUMENTS

| CN | 1243116 A | 2/2000 |
|---|---|---|
| WO | WO2005068405 A1 | 7/2005 |
| WO | 2010001456 A1 | 1/2010 |

OTHER PUBLICATIONS

All Office Actions: U.S. Appl. No. 15/225,865.
(Continued)

*Primary Examiner* — Tam M Nguyen
(74) *Attorney, Agent, or Firm* — Andrew J. Mueller

(57) ABSTRACT

The present invention relates generally to methods for producing detergent compounds from waste plastic feedstocks. More specifically, the invention relates to methods for producing detergent intermediates, including alkylbenzenes, paraffins, olefins, oxo alcohols, and surfactant derivatives thereof from waste plastic feedstock.

8 Claims, 8 Drawing Sheets

Related U.S. Application Data application No. 15/225,865, filed on Aug. 2, 2016, now Pat. No. 10,308,896.

(60) Provisional application No. 62/203,022, filed on Aug. 10, 2015.

(51) Int. Cl.

| | | |
|---|---|---|
| *C07B 41/04* | (2006.01) | |
| *C07B 45/04* | (2006.01) | |
| *C07C 2/66* | (2006.01) | |
| *C07C 5/32* | (2006.01) | |
| *C07C 303/02* | (2006.01) | |
| *C10G 1/00* | (2006.01) | |
| *C10G 1/10* | (2006.01) | |
| *C10G 3/00* | (2006.01) | |
| *C10G 45/00* | (2006.01) | |
| *C10G 45/02* | (2006.01) | |
| *C10G 65/04* | (2006.01) | |
| *C11D 1/37* | (2006.01) | |
| *C11D 17/04* | (2006.01) | |
| *C11D 1/14* | (2006.01) | |
| *C11D 1/29* | (2006.01) | |

(52) U.S. Cl.
CPC ............... *C07C 2/66* (2013.01); *C07C 5/32* (2013.01); *C07C 303/02* (2013.01); *C10G 1/002* (2013.01); *C10G 1/10* (2013.01); *C10G 3/42* (2013.01); *C10G 3/50* (2013.01); *C10G 45/00* (2013.01); *C10G 45/02* (2013.01); *C10G 65/04* (2013.01); *C11D 1/37* (2013.01); *C11D 17/042* (2013.01); *C11D 17/045* (2013.01); *C10G 2300/1003* (2013.01); *C10G 2400/00* (2013.01); *C11D 1/146* (2013.01); *C11D 1/29* (2013.01); *Y02P 30/20* (2015.11)

(56) References Cited

U.S. PATENT DOCUMENTS

| | | | | |
|---|---|---|---|---|
| 6,150,322 | A * | 11/2000 | Singleton | C11D 1/146 510/424 |
| 6,150,577 | A * | 11/2000 | Miller | C10G 1/10 585/734 |
| 6,589,927 | B1 | 7/2003 | Kott | |
| 7,202,205 | B1 * | 4/2007 | Connor | C11D 1/146 510/505 |
| 8,480,880 | B2 | 7/2013 | Miller | |
| 9,758,747 | B2 | 9/2017 | Boutique et al. | |
| 10,308,896 | B2 | 6/2019 | Scheibel | |
| 10,442,997 | B2 * | 10/2019 | Narayanaswamy | C10G 1/02 |
| 2009/0151233 | A1 | 6/2009 | Miller | |
| 2009/0158637 | A1 | 6/2009 | Mccall | |
| 2009/0318737 | A1 | 12/2009 | Luebke | |
| 2011/0065625 | A1 | 3/2011 | Boutique | |
| 2012/0151828 | A1 | 6/2012 | Kalnes | |
| 2012/0184787 | A1 * | 7/2012 | Miller | C10M 175/0025 585/1 |
| 2013/0152459 | A1 | 6/2013 | Banerjee et al. | |
| 2013/0253240 | A1 | 9/2013 | Bozzano | |
| 2013/0305591 | A1 | 11/2013 | Mccall et al. | |
| 2015/0232395 | A1 * | 8/2015 | Nyce | C07C 1/0435 585/329 |
| 2016/0068785 | A1 * | 3/2016 | Vinson | C11D 3/38636 510/340 |
| 2016/0264874 | A1 | 9/2016 | Narayanaswamy | |
| 2016/0264885 | A1 | 9/2016 | Narayanaswamy | |
| 2016/0362609 | A1 * | 12/2016 | Ward | C10G 69/02 |
| 2017/0044465 | A1 * | 2/2017 | Scheibel | C07C 5/32 |
| 2019/0161683 | A1 * | 5/2019 | Narayanaswamy | C10K 1/103 |
| 2019/0177626 | A1 * | 6/2019 | Ramamurthy | C10G 69/06 |
| 2019/0241838 | A1 | 8/2019 | Scheibel et al. | |
| 2021/0087473 | A1 * | 3/2021 | Pradeep | C10B 53/07 |

OTHER PUBLICATIONS

All Office Actions, U.S. Appl. No. 16/385,040, filed Apr. 16, 2019.
EPA: State of Practice for Emerging Waste Conversion Technologies Final Project Report, EPA/600/R-12/705 Oct. 2012.
PCT International Search Report for application No. PCT/US2016/1045219, dated Nov. 11, 2016, 11 pages.
A. Kayode Coker, "Glossary of Petroleum and Technical Terminology", Petroleum Refining Design and Applications Handbook, vol. 1, 2018 Scrivener Publishing LLC, Published 2018 by John Wiley & Sons, Inc.
Onwudili et al. "Composition of products from the pyrolysis of polyethylene and polystyrene in a closed batch reactor: Effects of temperature and residence time", Journal of Analytical and Applied Pyrolysis, vol. 86, Aug. 3, 2009, pp. 293-303.
Saptoadi et al. "Utilization of Plastics Waste Oil as Partial Substitute for Kerosene in Pressurized Cookstoves", International Journal of Environmental Science and Development, vol. 6, No. 5, May 2015, pp. 363-368.
Third Party Opposition filed for European Patent Application Ser. No. 16751430.6, Oct. 26, 2021; 24 pages.
E. Butler et al, "Waste Polyole fins to Liquid Fuels via Pyrolysis: Review of Commercial State-of-the-Art and recent Laboratory Research", Waste Biomass Valor, 2011; 2:227-255.
Fahim et al., Fundamentals of Petroleum Refining—chapter 4-crude distillation, Nov. 19, 2019, 26 Pages.
J.E. Shepherd et al; "Flash Point and chemical Composition of Aviation Kerosene (Jet A)", May 26, 2000, 38 Pages.
Speight et al, Fouling in Refineries—Chapter 2—Refinery Feedstocks, May 14, 2015, 35 Pages.

* cited by examiner

METHODS FOR PRODUCING ALKYLBENZENES, PARAFFINS, OLEFINS AND OXO ALCOHOLS FROM WASTE PLASTIC FEEDSTOCKS

FIELD OF THE INVENTION

The present invention relates generally to methods for producing detergent compounds from waste plastic feedstocks. More specifically, the invention relates to methods for producing detergent intermediates, including alkylbenzenes, paraffins, olefins, oxo alcohols, and surfactant derivatives thereof from waste plastic feedstock.

BACKGROUND OF THE INVENTION

While detergents made utilizing biodegradable surfactant intermediates, such as alkyl benzenes, 2-alkyl alcohols (e.g., Isalchem®, Sasol), and primarily linear alcohols (Neodol®, Shell), exist today, these surfactant intermediates are all made from conventional feedstocks, such as petroleum-derived ethylene, kerosene, or other petrol materials. There is also substantial use of fats and oils to product fatty alcohol-derived surfactant intermediates. There is also an ongoing effort to convert fats and oils and waste fats and oils to hydrocarbons for use in making surfactants. Waste plastic feedstocks, however, have not been identified as viable for conversion into surfactant intermediates and surfactants. Due to the growing environmental concerns over fossil fuel extraction, economic concerns over exhausting fossil fuel deposits, and the growing global problem of plastic waste in garbage dumps, waterways, and oceans, there is a need for an alternative use for plastic waste. As a feedstock, waste plastic has now been surprisingly found to have desirable properties for making surfactant intermediates, such as paraffins, olefins, alkylbenzenes, and oxo alcohols, and their corresponding surfactants for use in detergent products. The waste plastic converted by various processes to a waste plastic feedstock for the above materials may either be used alone or in combination with traditional surfactant feedstocks, such as kerosene, polyolefins derived from natural gas, coal, crude oil or even biomass, or waste fat/oil-derived paraffin and olefin, to produce biodegradable surfactants for use in detergents and other industries (thereby providing a benefit to society). The waste plastic is typically converted via pyrolysis to a waste plastic feedstock, thereby removing waste plastic from the environment.

Accordingly, there is a need to provide methods for producing linear and branched paraffins, linear and branched olefins, linear and branched alkyl benzenes, linear and branched oxo alcohols, linear and branched alkyl amines, and the surfactants derived from these surfactant intermediates (including blends of linear and branched intermediates) from a feed source that includes waste plastic feedstock, either alone or in combination with another feedstock(s), as disclosed herein, such as kerosene. It is also desirable to provide detergent ingredients made from waste plastic feedstock, either alone or in combination with another feedstock(s), as disclosed herein.

Moreover, it has been found that waste plastic feedstock has many desirable properties for producing linear and branched paraffins, linear and branched olefins, linear and branched alkyl benzenes, linear and branched oxo alcohols, linear and branched alkyl amines, and the surfactants derived from these surfactant intermediates (including blends of linear and branched intermediates), such as olefin and paraffin sulfonates, alkylbenzene sulfonate, and sulfates as well as ethoxylated sulfates derived from the oxo alcohols, as compared to traditional feedstock(s) used today and disclosed herein, e.g., kerosene feedstock.

SUMMARY OF THE INVENTION

The present invention attempts to solve one more of the needs by providing a method for producing paraffin from waste plastic feedstock and kerosene and/or another source(s) of hydrocarbons comprising the steps of: providing a first feed stream comprising kerosene and/or another source(s) of hydrocarbons; pre-fractionating the first feed stream to produce a first heart cut paraffin stream comprising paraffins in a heart cut range; combining the heart cut paraffin stream with a second feed stream comprising waste plastic feedstock to form a combined stream; hydrotreating the combined stream; fractionating the hydrotreated stream to remove paraffins that are heavier and/or lighter than the heart cut range to form a second heart cut paraffin stream; and optionally separating branched and cyclic hydrocarbons from the second heart cut paraffin stream to form a linear heart cut paraffin stream.

The present invention further relates to a method for producing olefin from waste plastic feedstock and kerosene and/or another source(s) of hydrocarbons, as disclosed herein, comprising the steps of: providing a first feed stream comprising kerosene and/or another source(s) of hydrocarbons; pre-fractionating the first feed stream to produce a first heart cut paraffin stream comprising paraffins in a heart cut range; combining the first heart cut paraffin stream with a second feed stream comprising waste plastic feedstock to form a combined stream; hydrotreating the combined stream; fractionating the hydrotreated stream and removing paraffins that are heavier and/or lighter than the heart cut range to form a second heart cut paraffin stream; optionally separating branched and cyclic hydrocarbons from the second heart cut paraffin stream; and dehydrogenating the optionally separated second heart cut paraffin stream to form a stream comprising olefins.

The present invention further relates to a method for producing paraffin from waste plastic feedstock comprising the steps of: providing a feed stream comprising waste plastic feedstock; pre-fractionating the feed stream to produce a first heart cut paraffin stream comprising paraffins in a heart cut range; hydrotreating the first heart cut paraffin stream; fractionating the hydrotreated feed stream and removing paraffins that are heavier and/or lighter than a heart cut range to form a second heart cut paraffin stream; optionally separating branched and cyclic hydrocarbons from the second heart cut paraffin stream to form a linear heart cut paraffin stream.

The present invention further relates to a method for producing olefin from waste plastic feedstock comprising: providing a feed stream comprising waste plastic feedstock; pre-fractionating the feed stream to produce a first heart cut paraffin stream comprising paraffins in a heart cut range; hydrotreating the first heart cut paraffin stream; fractionating the hydrotreated feed stream to remove paraffins that are heavier and/or lighter than a heart cut range to form a second heart cut paraffin stream; optionally separating branched and cyclic hydrocarbons from the second heart cut paraffin stream; dehydrogenating the optionally separated second heart cut paraffin stream to form a stream comprising olefins.

The present invention also relates to a method of producing linear alkylbenzenes, branched alkylbenzenes, or mixtures thereof derived from waste plastic feedstock alone or derived from a combination of waste plastic feedstock and kerosene and/or another source(s) of hydrocarbons, as well as surfactants derived from such alkylbenzenes (e.g., sulfonated linear alkylbenzene, sulfonated branched alkylbenzene, or mixtures thereof).

The present invention also relates to a method of producing linear oxo alcohols, branched oxo alcohols, or mixtures thereof derived from waste plastic feedstock alone or derived from a combination of waste plastic feedstock and kerosene and/or another source(s) of hydrocarbons as disclosed herein, as well as surfactants derived from such oxo alcohols Such surfactants include sulfated linear detergent alcohols, sulfated branched detergent alcohols, ethoxylated and sulfated linear detergent alcohols, ethoxylated sulfated branched detergent alcohols, ethoxylated linear detergent alcohols, ethoxylated branched detergent alcohols, or mixtures thereof.

The present invention also relates to a method of producing linear paraffin sulfonates, branched paraffin sulfonates, or mixtures thereof, as well as linear olefin sulfonates, branched olefin sulfonates, or mixtures thereof derived from waste plastic feedstock alone or derived from a combination of waste plastic feedstock and kerosene and/or another source(s) of hydrocarbons as disclosed herein.

The present invention also relates to a method of producing linear amines, branched amines, or mixtures thereof derived from waste plastic feedstock alone or derived from a combination of waste plastic feedstock and kerosene and/or another source(s) of hydrocarbons as disclosed herein, as well as surfactant derivatives of such amines, including linear or branched amine oxide.

The present invention also relates to a detergent composition comprising one or more of the surfactants produced according to the methods disclosed herein and methods of making such detergent compositions.

DETAILED DESCRIPTION OF THE INVENTION

Figure 1:
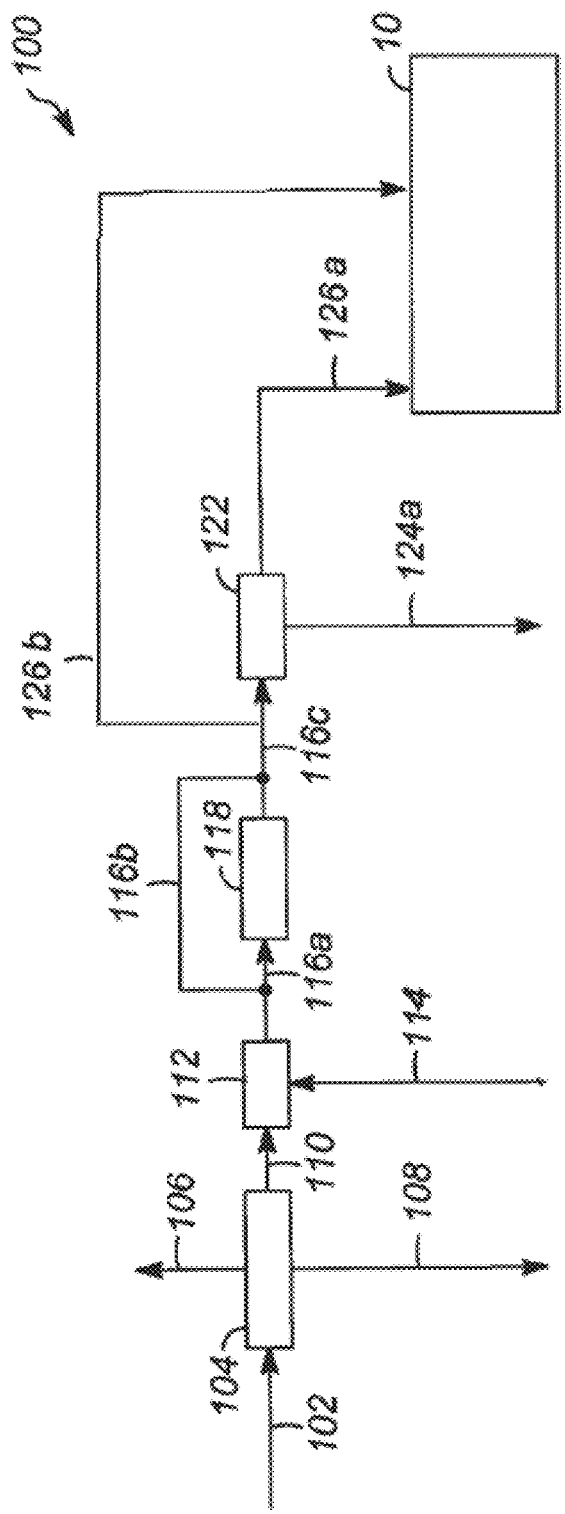
FIG. 1 schematically illustrates a system utilizing a process for producing alkylbenzenes, paraffins, and/or olefins from waste plastic feedstock and kerosene.

Features and benefits of the present invention will become apparent from the following description, which includes examples intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, articles such as "a" and "an" when used in a claim, are understood to mean one or more of what is claimed or described.

As used herein, the terms "include", "includes" and "including" are meant to be non-limiting.

As used herein, the term "waste plastic feedstock" means waste plastic that has been depolymerized via pyrolysis conditions, which may be catalytic or non-catalytic, continuous or batch.

As used herein, the term "LAS" refers to linear alkylbenzene sulfonate.

As used herein, the term "LAB" refers to linear alkylbenzene.

As used herein, the term "fatty alcohol" refers to a linear alcohol derived from natural oil via reduction of the oil to alcohol (specifically, transesterification of triglycerides to give methyl esters which in turn are hydrogenated to the alcohols). Fatty alcohols are essentially 100% linear.

As used herein, the term "detergent alcohol" is broader than the term fatty alcohol and encompasses fatty alcohols as well as synthetic alcohols. Detergent alcohols may be linear, branched, or a mixture thereof. For example, synthetic alcohols may contain varying levels of 2-alkyl branched content, depending on the process used to make the synthetic alcohols. Synthetic alcohols may also contain branched content due to the feedstock containing branched paraffins or olefins.

As used herein, the term "MTA" refers to metric tons annual.

As used herein, the term "paraffin sulfonate" refers to a surfactant derived from sulfoxidation of paraffins.

As used herein, the term "olefin sulfonate" refers to a surfactant derived from direct sulfonation of olefin.

The terms "kerosene-based" (as in "kerosene-based alkylbenzene") and "petrol-based" (as in "petrol-based alkylbenzene") are used interchangeably to refer to a material (or the production thereof) that is produced from kerosene or another petrochemical that is extracted from the earth, such as crude oil, natural gas, or ethylene oligomers derived from ethylene from various sources, such as natural gas, crude oil, coal, or the like. Any of these petrol-based feedstocks may be blended with a waste plastic feedstock to produce alkylbenzene, oxo alcohol, or any of the other surfactant intermediates or surfactants disclosed herein.

The term "another source(s) of hydrocarbon" includes feedstock derived from natural gas, crude oil, coal, biomass, fats or oils, or waste fats or oils. Feedstocks derived from natural gas, crude oil, coal, biomass, fats or oils, or waste fats or oils contain a hydrocarbon stream similar to that of kerosene or an olefin stream. For example, the Neodene® products sold by Shell include linear alpha and internal olefins that are made via ethylene. Other olefins, such as alpha olefins, may come from processes known to one skilled in the art, such as Ziegler chemistry. Another source of olefins may be vinylidene-type, which may come from short chain olefin dimerization (also known to one skilled in the art) and may be blended with waste plastic-based olefins and/or paraffins.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

The methods and systems disclosed herein relate to producing linear or branched alkylbenzene, linear or branched paraffin, linear or branched olefin, and/or linear or branched oxo alcohol from waste plastic feedstock alone or waste plastic feedstock in combination with kerosene and/or another source(s) of hydrocarbons, as disclosed herein. The methods and systems disclosed herein provide an alternative use for waste plastic, which may otherwise end up in landfills or in the environment. The waste plastic feedstock is made by pyrolyzing waste plastic, either catalytically or non-catalytically and via a continuous or a batch process. The pyrolysis of waste plastic is well known in the art. Multiple variations of pyrolysis are practiced to produce waste plastic feedstocks. The following are non-limiting examples of companies that are piloting waste plastic pyrolysis, practicing it commercially, or selling equipment to pyrolize waste plastic to produce a feedstock for fuel or chemical use: PARC; Resynergi; Vadxx; Green Enviro Tech Holdings; J.U.M Global; ReGEN Fuels and Energy LLC; Green Mantra Technologies; Climax Global Energy; Envion; Nexus Fuels;JBI, Inc.; Recarbon Corp; Anhui Oursun Environmental Technologies; ECO Int'l Marketing; P-fuel, ltd.; Polymer Energy; PLastOil; Promeco; T Technology; ROYCO FUEL CHINA; AYU Global Resources, Inc. and Plastic2Fuel.

The waste plastic used in the various available pyrolysis processes is derived from plastics designated by #1-#6). It may be desirable to use plastic waste designated by #1, #2, #4 and #6, though all grades may be used depending on the nature of the pyrolysis and subsequent processing steps.. # 1 plastic waste is polyethylene terephthalate, #2 plastic waste is high density polyethylene, #4 plastic waste is low density polyethylene), and #5 plastic waste is polypropylene. If, for example, a pyrolysis plant desires to produce a waste plastic feedstock having a low sulfur, oxygen, and nitrogen content, then), then #2, #4, and #5 plastic wastes may be most desirable. If a pyrolysis plant desires to minimize the aromatic content of the pyrolyzed product, then reducing #1 plastic waste and #6 plastic waste may achieve lower levels of aromatics in the product of the pyrolysis process. Other plastics, such as #3 (PVC), may also be used but require additional processing units to remove the chlorine produced by pyrolysis.

Plastics in category #7 (unknown material) may also be used, particularly if the #7 plastic waste is identified as containing #2 plastic waste, #4 plastic waste, #5 plastic waste, a mixture or copolymer thereof, or a mixture or copolymer of polyethylene and polypropylene. #7 plastic waste may not be recycled because of its unusual size of a #7 container, because the #7 plastic waste comes from industrial. When the #7 plastic waste contains other materials, such as polyacrylonitrile, polyacrylic acid, polyvinyl sulfonate, which can introduce undesirable impurities (e.g., nitrogen, oxygen, sulfur), these impurities may be managed by a hydrotreatment unit in a LAB and/or LAB/oxo alcohol facility (e.g., if the impurity content is deemed to be low for the particular facility).

It has been found that the waste plastic feedstock may produce an increased level of linear paraffin and linear olefin, as compared to petroleum-based kerosene feedstock. Also, the sulfur, oxygen, and nitrogen content of the waste plastic feedstock may be reduced, depending on the type(s) of plastic waste that are used; a reduced content of sulfur, oxygen, and nitrogen may be advantageous for a feed stream entering a linear alkylbenzene plant or a combined linear alkylbenzene and oxo alcohol plant or for other surfactant intermediates and surfactants.

Paraffin and olefin are key feedstocks for alkylbenzene and oxo alcohols. When linear alkylbenzene was first produced in the 1960s, it contained an increased content of linear paraffins and linear olefins (from light crude oil), as described in the literature. Over the past 50 years, crude oil has come to include heavier crude, which requires more aggressive processing and thus contains less linear paraffin and linear olefin, which results in lower throughput in processing plants that convert kerosene to linear alkylbenzene and oxo alcohols. By supplementing kerosene and/or another source(s) of hydrocarbons with a waste plastic feedstock source or by using a waste plastic feedstock source alone, a producer can greatly increase the throughput in a linear alkylbenzene plant or oxo alcohol production, in the case of a plant that produces both linear alkylbenzene and oxo alcohol, thereby improving the efficiency of the process, and the surfactant made from such waste plastic-derived linear alkylbenzene or oxo alcohol may then be used to make detergent formulations for consumers.

One may also use both the linear and branched feedstocks derived from waste plastic alone or waste plastic in combination kerosene and/or another source(s) of hydrocarbons to make linear and/or branched mixtures of alkylbenzenes, oxo alcohols, and surfactants derived therefrom.

Table 1, below, shows an illustration of the benefits that may be realized by supplementing a kerosene feed with waste plastic feedstock (Example 1 versus Example 2). Table 1 also illustrates an example that uses 100% waste plastic feedstock (Example 3). Table 1 is provided merely for illustration, and is not limiting on the possible benefits, compositions, or plastic waste-derived feed/kerosene feed amounts realizable in accordance with the present disclosure. The information in Table 1 is calculated based on potential production volumes and analysis of a typical kerosene feedstock and a waste plastic feedstock, using the 2D-GC/TOFMS and GC methods described herein.

TABLE 1

| Feed Type | Example 1 | Example 2 | Example 3 |
|---|---|---|---|
| Heart Cut Waste Plastic Pyrolysate in MTA | 65182 | 0 | 133,149 |
| Kerosene in MTA | 229883 | 500,000 | 0 |
| TOTAL MTA Feeds | 295065 | 500,000 | 133,149 |
| Extract MTA (linear paraffin) | 70085 | 70085 | 70085 |
| Product Purity | 0.985 | 0.985 | 0.985 |
| Product Aromatics | 0.005 | 0.005 | 0.005 |
| Product C# Distribution | | | |
| nC9 | 0 | 0 | 0 |
| nC10 | 10.00 | 15.21 | 13.84 |
| nC11 | 32.32 | 33.32 | 28.37 |
| nC12 | 30.11 | 28.36 | 28.86 |
| nC13 | 26.96 | 22.69 | 28.29 |
| nC14 | 0.61 | 0.43 | 0.72 |
| AMW Target Range | 166.95 | 168.2 | 166.8 |

As shown in Table 1, in Example 1, 65,182 MTA of waste plastic feedstock (heart cut) are provided with 229883 MTA kerosene feed. In Example 2, however, a greater amount of MTA, 500,000 MTA, is needed to achieve a similar production quantity of linear paraffin, when only heart cut kerosene feed is used. Example 3 shows the production quantity of linear paraffin produced from waste plastic feedstock alone. Thus, Table 1 shows that by blending waste plastic feedstock in the heart cut range with kerosene, the same production quantity of linear paraffin may be obtained while using about 40% less total feedstock in the production facility. Example 3 shows that by using waste plastic feedstock (heart cut) alone, the same amount of linear paraffin product may be produced using about 28% of the amount of feedstock as compared to using kerosene feedstock alone. In other words, more than 3.5 times as much linear paraffin can be produced using waste plastic feedstock (heart cut) alone.

Table 2 shows an analysis of waste plastic feedstock (derived from plastic waste via pyrolysis) in the heart cut range (middle distillate) and an analysis of a kerosene feedstock in the heart cut range. Table 2 also shows the analysis for a hydrotreated sample of waste plastic feedstock (middle distillate). Table 2 shows that the conversion of olefin in the original middle distillate fraction of the waste plastic feedstock has almost doubled the linear paraffin content as compared to the kerosene feedstock, which has less linear olefin to contribute to total paraffin after hydrotreatment. The compositions in Table 2 are non-limiting examples of compositions and the content of olefins and paraffins, linear and branched, and aromatics, as identified by the 2D-GC/TOFMS method described herein. The information in Table 2 is calculated based on the analysis of a typical kerosene feedstock and a waste plastic feedstock, using the 2D-GC/TOFMS and GC methods described herein. The information in Table 2 is reported in GC area %. Average chain length is calculated from the GC area %.

TABLE 2

Analysis of waste plastic feedstock compared to Petrol Kero K1

| Compound Class | Petrol Derived Kerosene K1 (from Sunoco) | Waste Plastic Feedstock Middle Distillate | Waste Plastic Feedstock Middle distillate hydrotreated |
|---|---|---|---|
| Linear Paraffin | 24.2 | 25.5 | 57.9 |
| Total Paraffin | 58.0 | 29.9 | 72.5 |
| Linear Olefin | 4.7 | 28.0 | 1.7 |
| Total Olefin + Cyclics | 27.0 | 60.9 | 17.1 |
| Aromatic | 15.0 | 9.1 | 6.4 |
| Phenol | None Detected | 0.1 | 0.2 |
| Branched Hydrocarbons | 33.8 | 14.8 | 20.1 |
| Ave chain length for linear paraffin composition | 12.4 | 15.1 | 15.0 |
| Total Potential Linear Paraffin post hydrotreatment | 29.0 | 61.5 | 57.9 |

Methods for Producing Surfactant Intermediates and Surfactants Derived from Waste Plastic Feedstock The present invention relates to improved, highly efficient processes for making surfactant intermediates and surfactants, which may be used in various cleaning products. More specifically, the present invention relates to methods and systems for producing a linear alkylbenzene, paraffin, or olefin from waste plastic feedstock alone or in combination with a kerosene feedstock.

In addition to the sustainability benefits of using waste plastic feedstock (e.g., removal of waste plastic from the environment), it has been found that waste plastic feedstock has very desirable properties for making surfactant intermediates, such as alkylbenzene and oxo alcohols. For example, waste plastic feedstock has a much greater content of linear paraffin than traditional kerosene feedstock; waste plastic feedstock has a greater content of linear olefin; it has a reduced content of aromatics, sulfur, and oxygen components. These properties provide for a desirable feedstock, which can either be used alone or blended with kerosene feedstock.

A method for producing a paraffin from a waste plastic feedstock in combination with kerosene and/or another suitable source(s) of hydrocarbons as defined herein may include providing a first feed stream comprising kerosene and/or another suitable source(s) of hydrocarbons, pre-fractionating the first feed stream to produce a heart cut paraffin stream comprising paraffins in a heart cut range, and combining the heart cut paraffin stream with a second feed stream comprising waste plastic feedstock to form a combined stream. The method may further include one or more of the steps of hydrotreating the combined stream, fractionating the hydrotreated stream to remove paraffins that are heavier and/or lighter than the heart cut range to form a second heart cut paraffin stream, and separating branched and cyclic hydrocarbons from the second heart cut paraffin stream to form a linear heart cut paraffin stream. Hydrotreating is a well known process that removes oxygen, nitrogen, and sulfur and also reduces any remaining olefins to paraffins. The waste plastic feedstock may also be pre-fractionated to provide a heart cut stream of waste plastic feedstock prior to combining the waste plastic feedstock stream with the kerosene-based heart cut stream. When the method for producing paraffin from waste plastic feedstock in combination with kerosene and/or another suitable source(s) of hydrocarbons includes the separating step, the paraffin product is linear, as branched and cyclic hydrocarbons are removed via the separating step. The separating step may optionally produce two streams of paraffins—branched paraffins and linear paraffins. When the method for producing paraffin from waste plastic feedstock in combination with kerosene and/or another suitable source(s) of hydrocarbons does not include the optional separating step, the paraffin product is a blend of linear, branched, and cyclic paraffins.

A method for producing paraffin from a waste plastic feedstock alone may include providing a feed stream comprising waste plastic feedstock and pre-fractionating the feed stream to produce a first heart cut paraffin stream comprising paraffins in a heart cut range. The method may further include one or more of the steps of hydrotreating the first heart cut paraffin stream, fractionating the hydrotreated feed stream to remove paraffins that are heavier and/or lighter than the heart cut range to form a second heart cut paraffin stream, separating branched and cyclic hydrocarbons from the second heart cut paraffin stream to form a linear heart cut paraffin stream. When the method for producing paraffin from waste plastic feedstock alone includes the optional separating step, the paraffin product is linear, as branched and cyclic hydrocarbons are removed via the separating step. The separating step may optionally produce two streams of paraffins—branched paraffins and linear paraffins. When the method for producing paraffin from waste plastic feedstock does not include the optional separating step, the paraffin product is a blend of linear, branched, and cyclic paraffins.

A method for producing an olefin from waste plastic feedstock in combination with kerosene and/or another suitable source(s) of hydrocarbons may include providing a first feed stream comprising kerosene and/or another suitable source(s) of hydrocarbons, pre-fractionating the first feed stream to produce a first heart cut paraffin stream comprising paraffins in a heart cut range, and combining the first heart cut paraffin stream with a second feed stream comprising waste plastic feedstock to form a combined stream. The method may further include the steps of hydrotreating the combined stream, fractionating the hydrotreated stream to remove paraffins that are heavier and/or lighter than the heart cut range to form a second heart cut paraffin stream, separating branched and cyclic hydrocarbons from the second heart cut paraffin stream, and dehydrogenating the (optionally separated) second heart cut paraffin stream to form a stream comprising olefins. When the method for producing olefin includes the optional separating step, namely separation of linear paraffin from branched and cyclic paraffin, the step of dehydrogenating produces linear olefins, which may be desirable for some oxo alcohols and for linear alkylbenzene production. When the method for producing olefin does not include the optional separating step, the step of dehydrogenating produces a blend of linear, branched, and cyclic olefins.

A method for producing an olefin from waste plastic feedstock alone may include providing a feed stream comprising waste plastic feedstock and pre-fractionating the feed stream to produce a first heart cut paraffin stream comprising paraffins in a heart cut range. The method may further include one or more of the steps of hydrotreating the first heart cut paraffin stream, fractionating the hydrotreated feed stream to remove paraffins that are heavier and/or lighter than the heart cut range to form a second heart cut paraffin stream, separating branched and cyclic hydrocarbons from the second heart cut paraffin stream, and dehydrogenating the (optionally separated) second heart cut paraffin stream to form a stream comprising olefins. When the method for producing olefin includes the optional separating step, namely separation of linear paraffin from branched and cyclic paraffin, the step of dehydrogenating produces linear olefins, which may be desirable for some oxo alcohols and for linear alkylbenzene production. When the method for producing olefin does not include the optional separating step, the step of dehydrogenating produces a blend of linear, branched, and cyclic olefins.

A method for producing a alkylbenzene from waste plastic feedstock in combination with kerosene and/or another suitable source(s) of hydrocarbons may include providing a first feed stream comprising kerosene and/or another suitable source(s) of hydrocarbons, pre-fractionating the first feed stream to produce a first heart cut paraffin stream comprising paraffins in a heart cut range, and combining the first heart cut paraffin stream with a second feed stream comprising waste plastic feedstock to form a combined stream. The waste plastic feedstock may also be pre-fractionated to provide a heart cut stream of waste plastic feedstock prior to combining. This pre-fractionating may be performed at the site where the waste plastic feedstock is produced or at the site where the alkylbenzene is produced. The method may further include one or more of the steps of hydrotreating the combined stream, fractionating the hydrotreated stream to remove paraffins that are heavier and/or lighter than the heart cut range to form a second heart cut paraffin stream, dehydrogenating the second heart cut paraffin stream to form a stream comprising olefins, and alkylating the stream comprising olefins with a third feed stream comprising benzene to form a stream comprising alkylbenzenes that are linear, branched, or a mixture thereof. The aromatic portion may be derived from a traditional petroleum-based feedstock. Alternatively, the aromatic portion may be derived from a renewable feedstock, e.g., natural oil, or from the naphtha fraction of waste plastic feedstock.

A method for producing alkylbenzene from waste plastic feedstock alone may include providing a feed stream comprising waste plastic feedstock, pre-fractionating the feed stream comprising waste plastic feedstock to produce a first heart cut paraffin stream comprising paraffins in a heart cut range. The method may further include one or more of the steps of hydrotreating the first heart cut paraffin stream, fractionating the hydrotreated stream to remove paraffins that are heavier and/or lighter than the heart cut range to form a second heart cut paraffin stream, dehydrogenating the second heart cut paraffin stream to form a stream comprising olefins, and alkylating the stream comprising olefins with a third feed stream comprising benzene to form a stream comprising alkylbenzenes that are linear, branched, or a mixture thereof. Thus, the non-aromatic portion of the alkylbenzene is derived from plastic waste. The aromatic portion may be derived from a traditional petroleum-based feedstock. Alternatively, the aromatic portion may be derived from a renewable feedstock, e.g., natural oil, or from the naphtha fraction of waste plastic feedstock.

A method for producing an oxo alcohol from waste plastic feedstock in combination with kerosene and/or another suitable source(s) of hydrocarbons may include providing a first feed stream comprising kerosene and/or another suitable source(s) of hydrocarbons, pre-fractionating the first feed stream to produce a first heart cut paraffin stream comprising paraffins in a heart cut range, and combining the first heart cut paraffin stream with a second feed stream comprising waste plastic feedstock to form a combined stream. The waste plastic feedstock may also be pre-fractionated to provide a heart cut stream of waste plastic feedstock prior to combining; this pre-fractionating may be performed at the site where the waste plastic feedstock is produced or at the site where the oxo alcohol is produced. The method may further include one or more of the steps of hydrotreating the combined stream, fractionating the hydrotreated stream to remove paraffins that are heavier and/or lighter than the heart cut range to form a second heart cut paraffin stream, dehydrogenating the second heart cut paraffin stream to form a stream comprising olefins, and hydroformylating the stream comprising olefins in the presence of syngas to form a stream comprising oxo alcohols that are linear, branched, or a mixture thereof. The oxo alcohols may be further purified by known means in the art. Alternatively, this method for producing an oxo alcohol may utilize waste plastic feedstock alone (without kerosene) to produce an oxo alcohol that is derived from only waste plastic feedstock and syngas (produced by any means).

A method for producing oxo alcohol from waste plastic feedstock alone may include providing a feed stream comprising waste plastic feedstock, pre-fractionating the feed stream comprising waste plastic feedstock to produce a first heart cut paraffin stream comprising paraffins in a heart cut range. The method may further include one or more of the steps of hydrotreating the first heart cut paraffin stream, fractionating the hydrotreated stream to remove paraffins that are heavier and/or lighter than the heart cut range to form a second heart cut paraffin stream, dehydrogenating the second heart cut paraffin stream to form a stream comprising olefins, and hydroformylating the stream comprising olefins in the presence of syngas to form a stream comprising oxo alcohols that are linear, branched, or a mixture thereof.

In FIG. 1, a system 100 utilizing an example process for producing a linear alkylbenzene, paraffin, and/or olefin is shown. A feedstock containing kerosene and/or another source(s) of hydrocarbons 102 is fed into a pre-fractionator 104. The pre-fractionator 104 fractionates the kerosene feed 102 into three streams 106, 108, and 110 product. Stream 106 is a light hydrocarbon stream that may include $C_9$ hydrocarbons and lighter hydrocarbons (hydrocarbons having fewer carbons) that are separated from the kerosene feed 102. Or, stream 106 may include $C_8$ and lighter hydrocarbons, or $C_{10}$ and lighter hydrocarbons, depending on the desired product composition of linear alkylbenzenes, paraffins, and olefins. Stream 108 is a distillate, or heavy hydrocarbon stream, that may include $C_{14}$ and heavier hydrocarbons (hydrocarbons having more carbons) that are separated from the kerosene feed 102. Or stream 108 may include anywhere from $C_{13}$-$C_{19}$ and heavier hydrocarbons, depending on the desired product composition of linear alkylbenzenes, paraffins, and olefins. Stream 110 includes hydrocarbons that are selected for further processing into the desired linear alkylbenzenes, paraffins, and olefins, and is referred to as the "heart cut." The heart cut stream 110 may include $C_{10}$-$C_{13}$ hydrocarbons that are separated from the kerosene feed 102. Or, stream 110 may include C10-$C_{18}$ hydrocarbons. Generally, the heart cut may include any range of hydrocarbons within the $C_9$-$C_{19}$ range. Light hydrocarbon stream 106 and distillate stream 108 are removed from the system 100 and may be used in other processes.

In FIG. 1, the heart cut stream 110 continues within system 100 for further processing in a kero-hydrotreater (KHT) 112. Hydrotreatment (also referred to as hydroprocessing) is a class of catalytic processes that comprise a set of reactions. Hydrotreating generally employs mild temperature and hydrogen pressures, such that only the more unstable compounds that might lead to the formation of gums, or insoluble materials, are converted to more stable compounds. Hydrotreament is used to substantially remove sulfur, oxygenates, nitrogen, and aromatics. KHT 112 is employed to treat the heart cut stream of hydrocarbons 110 to reduce the naturally occurring nitrogen and sulfur content in kerosene to acceptable levels for use in detergents and also to hydrogenate any olefins present in the feed. KHT 112 is a catalyst-based apparatus, and various catalysts (hydrotreating catalysts) for denitrification and desulfurization are known to those having ordinary skill in the art. In FIG. 1, the KHT 112 also receives a feed stream of waste plastic feedstock 114. In examples where, as in FIG. 1, the waste plastic feedstock feed 114 and the kerosene heart cut 110 are combined in the KHT 112, the KHT is also configured to hydrotreat the waste plastic feedstock and kerosene blend, which may contain some level of oxygen, sulfur, or nitrogen, depending on the kerosene feed and the source of the waste plastic for the waste plastic feedstock 114. Waste plastic feedstock 114 typically contains olefins, unless it is hydrotreated prior to entering the system. Thus, the KHT apparatus 112 may produce paraffins, by using a catalyst that is suitable for hydrogenation, deoxygenation, and denitrification/desulfurization or a mix of catalysts that each accomplish one or more of hydrogenation, deoxygenation, denitrification/desulfurization. A suitable KHT 112 apparatus for use is sold by UOP LLC and others.

A treated stream of paraffins 116a exiting KHT 112 may be fed to a separator 118 to separate the desirable linear paraffins from branched or cyclic compounds that may be included in the stream 116a. A suitable separator for this purpose is a separator that operates using the UOP LLC Molex® process, which is a liquid-state separation of normal paraffins from branched and cyclic components using UOP LLC Sorbex® technology. Other separators known in the art are suitable for use herein as well. Depending on the composition of the kerosene feed 102 and/or the waste plastic feedstock feed 114, separation of linear paraffins from branched and cyclic paraffins may not be necessary, and a treated stream of paraffins 116b from the KHT 112 may be directed downstream for further processing to produce linear and branched surfactant intermediates and linear and branched surfactants.

.A linear paraffin stream 116c exiting the separator 118, or the hydrotreated stream of linear and branched paraffins 116b, is fed to a fractionator 122. As discussed above, the pre-fractionator 104 removed light and heavy hydrocarbons from the kerosene feed 102; however, the waste plastic feedstock feed 114 may include hydrocarbons that are heavier and/or lighter than the heart cut range, and as such the fractionator 122 is optionally provided to fractionate hydrocarbons that are heavier and/or lighter than the desired heart cut range. Hydrocarbons that are C14 and heavier may be removed from system 100 in a heavy paraffins stream 124, and may be used in other processes, as in stream 108. Alternatively, hydrocarbons anywhere in the range from C15-C18 and heavier may be removed from system 100 in the heavy paraffins stream 124. The paraffins in the desired heart cut range exit the fractionator 122 in a stream 126a for further processing into alkylbenzene, paraffin, and/or olefin products in subsystem 10, as will be described in greater detail below.

Alternatively, if the waste plastic feedstock feed 114 does not require fractionation, then the stream 126b may be directed downstream for further processing.

Figure 6:
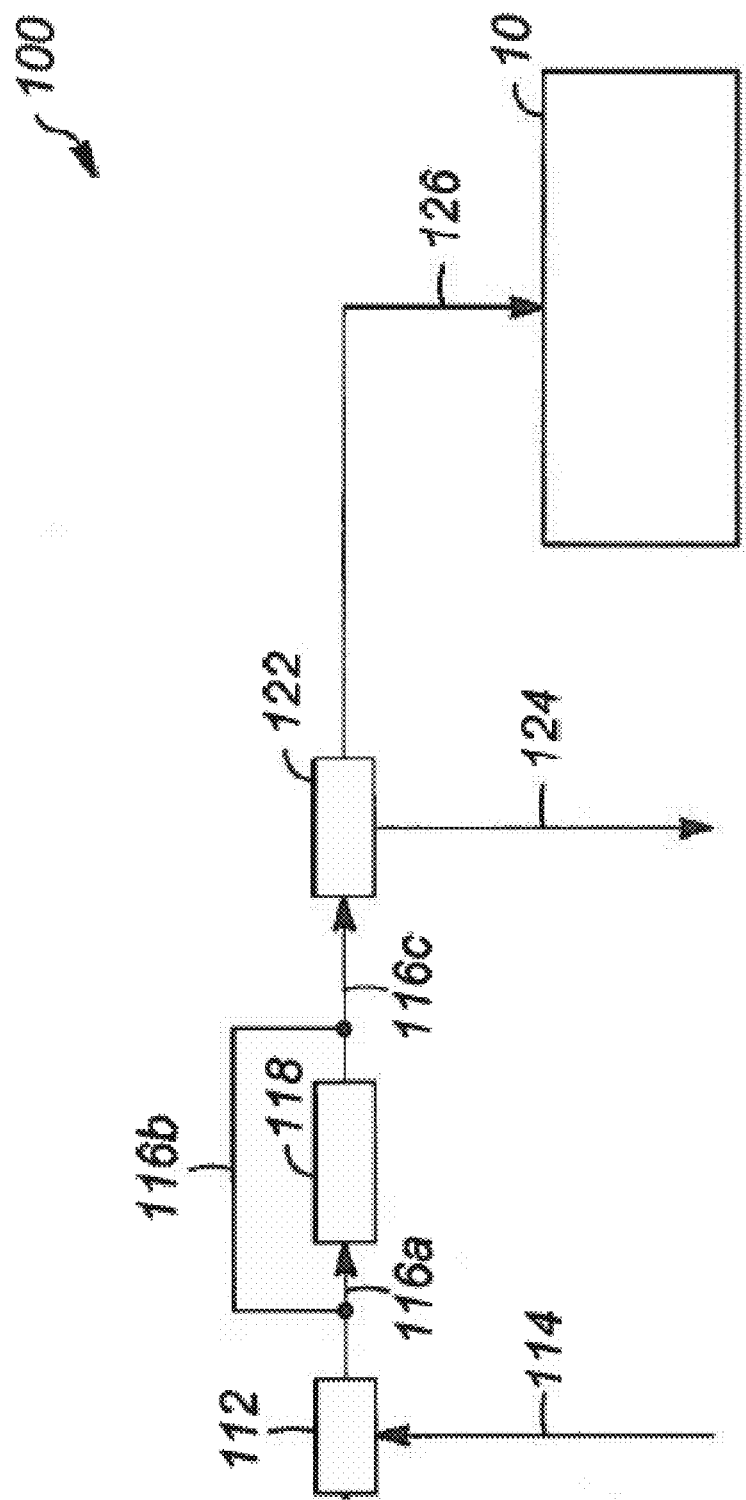

Alternatively, waste plastic feedstock 114 may be used as the only feedstock and not blended with any other feedstock (thereby eliminating feedstock 102 and process 104 in FIG. 1. FIG. 6 illustrates and example of such a process. All the numbers shown in FIG. 6 are the same as the numbers in FIG. 1 and are assigned the same meanings as in FIG. 1 (described above).

Figure 2:
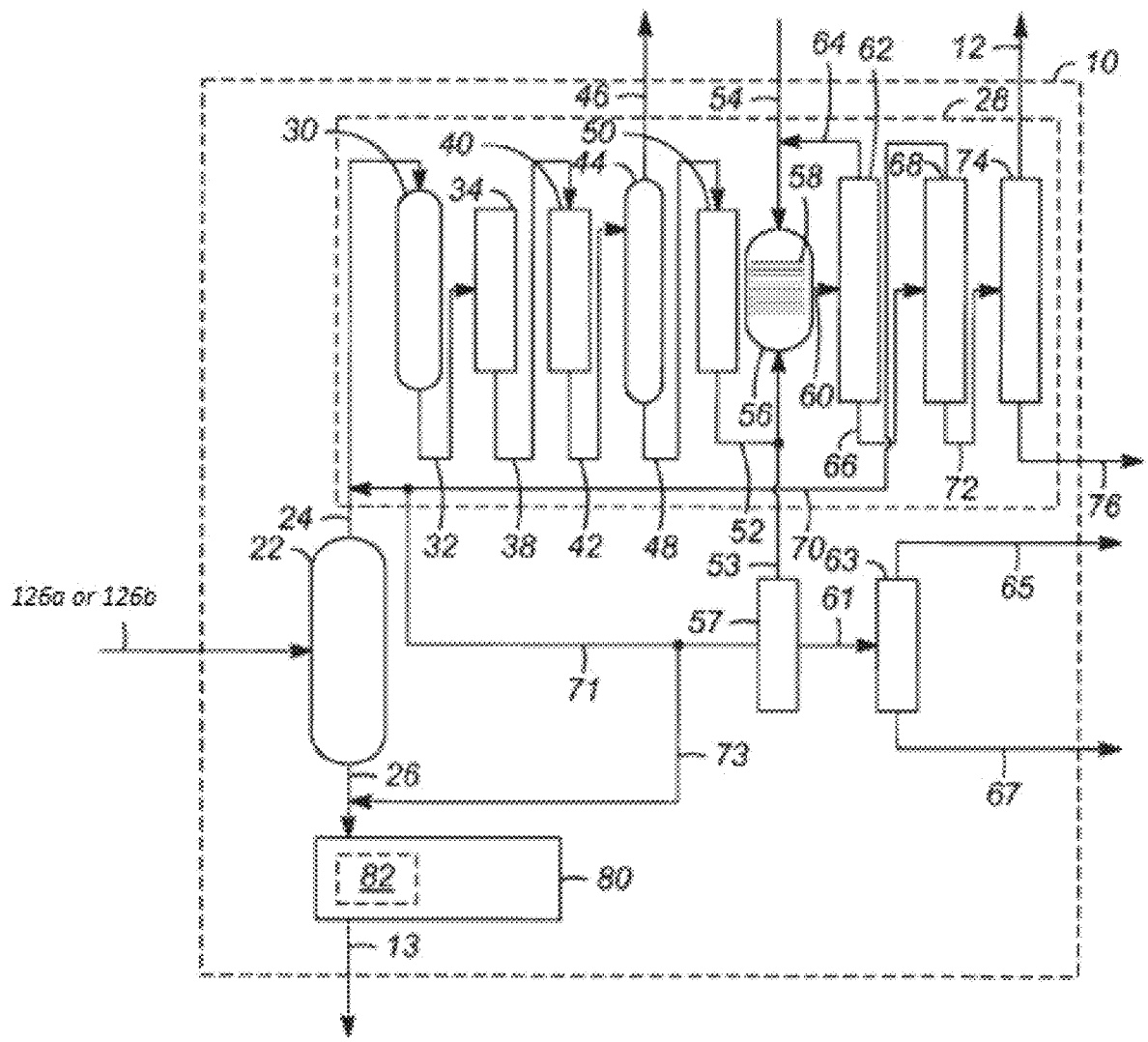
FIG. 2 schematically illustrates a subsystem of the system shown in FIG. 1 for producing alkylbenzenes, paraffins, and/or olefins.

In FIG. 2, a subsystem 10 utilizing a process for producing a linear and/or branched alkylbenzene, linear and/or branched paraffin, or linear and/or branched olefin is depicted. Subsystem 10 receives as its feed stream the stream 126a from the fractionator 122 or stream 126b, which is not fractionated, including the heart cut linear paraffins. Stream 126a or stream 126b is fed to a separator 22. The separator 22 may be a multi-stage fractionation unit, distillation system, or similar known apparatus. The separator 22 provides a means to separate the paraffins into various desirable fractions or into various portions for producing one or more of linear and/or branched alkylbenzenes, linear and/or branched paraffins, linear and/or branched olefins, or linear and/or branched oxo alcohols (with further processing). For example, as shown in FIG. 2, a first portion of paraffins 24 and a second portion of paraffins 26 are illustrated, although any number of paraffin portions may be provided. Portion 24 may include the same hydrocarbon range as portion 26, or they may be separated into different fractions. For example, where the heart cut is selected as C10-C18, portion 24 may include C10- C13 paraffins, whereas portion 26 may include C14- C18 paraffins. Alternatively, they may both include C10- C18 paraffins. In another example, where the heart cut is selected as C10-C13, both portions 24 and 26 may include hydrocarbons in that range. Numerous other examples are possible, depending on the quantity and the hydrocarbon content of the desired linear alkylbenzenes, paraffins, olefins, or oxo alcohols (produced downstream of subsystem 10). For example, it may be desirable to provide a $C_{10}$-$C_{13}$ heart cut fraction or a $C_{10}$-$C_{12}$ heart cut fraction and also provide a $C_{14}$-$C_{15}$ (two carbon-cut) fraction or a $C_{13}$-$C_{14}$ (two carbon-cut) fraction, respectively, which may be further processed downstream of subsystem 10 to make an oxo alcohol, using a known two carbon-cut process.

Either or both paraffin portions 24 or 26 (or other portions, if more are present) may thereafter be purified to remove trace contaminants, resulting in a purified paraffin product. When only paraffin production is desired, the entire paraffin product (i.e., all of the one or more portions) may be purified at this stage. Alternatively, some of the paraffin product may be directed to further processing stages for the production of alkylbenzenes and/or olefins. Alternatively, when only olefin and/or alkylbenzene production is desired, the entire paraffin product (i.e., all of the one or more portions) may be directed to further processing stages. As shown in the example subsystem 10 illustrated in FIG. 2, the second paraffin portion 26 is directed to a purification system 80 to remove any remaining trace contaminants, such as oxygenates, nitrogen compounds, and sulfur compounds, among others, that were not previously removed in the processing steps described above. In one example, purification system 80 is an adsorption system. Alternatively or additionally, a PEP unit 82, available from UOP LLC, may be employed as part of purification system 80. Subsequent to purification, a purified paraffin stream 13 may be removed from subsystem 10 as the paraffin product. As further shown in FIG. 2, the first portion of paraffins 24 (e.g., that portion of paraffins directed for further processing to alkylbenzenes and/or olefins, when desired) may be introduced to an alkylbenzene and olefin production zone 28. Specifically, the first portion of paraffins 24 may be fed into a dehydrogenation unit 30 in the alkylbenzene and olefin production zone 28. In the dehydrogenation unit 30, the first portion of paraffins 24 is dehydrogenated into mono-olefins of the same carbon numbers as the first portion of paraffins 24. Typically, dehydrogenation occurs through known catalytic processes, such as the commercially popular Pacol® process. Conversion is typically less than 30%, for example less than 20%, leaving greater than 70% paraffins unconverted to olefins. Di-olefins (e.g., dienes) and aromatics may also be produced, as expressed in the following equations:

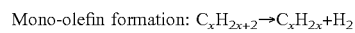

Mono-olefin formation: $C_xH_{2x+2} \rightarrow C_xH_{2x} + H_2$

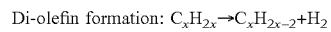

Di-olefin formation: $C_xH_{2x} \rightarrow C_xH_{2x-2} + H_2$

Aromatic formation: $C_xH_{2x-2} \rightarrow C_xH_{2x-6} + 2H_2$

In FIG. 2, a dehydrogenated stream 32 may exit the dehydrogenation unit 30 comprising mono-olefins and hydrogen, unconverted paraffins, as well as some di-olefins and aromatics. The dehydrogenated stream 32 is delivered to a phase separator 34 for removing the hydrogen from the dehydrogenated stream 32. The removed hydrogen can be directed away from system 100, or it can be used as fuel or as a source of hydrogen ($H_2$) for a hydrotreatment process.

At the phase separator 34, a liquid stream 38 is formed and includes the mono-olefins, the unconverted paraffins, and any di-olefins and aromatics formed during dehydrogenation. The liquid stream 38 exits the phase separator 34 and enters a selective hydrogenation unit 40. The hydrogenation unit 40 may be a DeFine® reactor (or a reactor employing a DeFine® process), available from UOP LLC. The hydrogenation unit 40 selectively hydrogenates at least a portion of the di-olefins in the liquid stream 38 to form additional mono-olefins. As a result, an enhanced stream 42 is formed with an increased mono-olefin concentration.

As shown, the enhanced stream 42 may pass from the hydrogenation unit 40 to a light hydrocarbons separator 44, such as a stripper column, which removes a light end stream 46 containing any light hydrocarbons, such as butane, propane, ethane and methane, which may result from cracking or other reactions during upstream processing. With the light hydrocarbons 46 removed, stream 48 is formed and may be delivered to an aromatic removal apparatus 50, such as a PEP unit available from UOP LLC. As indicated by its name, the aromatic removal apparatus 50 removes aromatics from the stream 48 and forms a stream of mono-olefins and unconverted paraffins 52.

In FIG. 2, to produce alkylbenzenes, the stream of mono-olefins 52 and a stream of benzene 54 are fed into an alkylation unit 56. The benzene may be sourced from petroleum, it may be sourced from renewable feedstocks described in the art, or it may be obtained from known processes for isolating benzene from waste plastic feedstocks that are referred to as naphtha grade. Furthermore the benzene may be sourced via waste plastic pyrolysis in the waste plastic pyrolysis naphtha fraction. The alkylation unit 56 holds a catalyst 58, such as a solid acid catalyst, which supports alkylation of the benzene 54 with the mono-olefins 52. Hydrogen fluoride (HF) and aluminum chloride ($AlCl_3$) are two major catalysts in commercial use for the alkylation of benzene with mono-olefins and may be used in the alkylation unit 56. Additional catalysts include zeolite-based or fluoridate silica alumina-based solid bed alkylation catalysts (for example, FAU, MOR, UZM-8, Y, X RE exchanged Y, RE exchanged X, amorphous silica-alumina, and mixtures thereof, and others known in the art). As a result of alkylation, alkylbenzene, typically called alkylbenzene (LAB), may be formed according to the reaction:

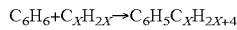

and may be present in the alkylation effluent 60. To optimize the alkylation process, surplus amounts of benzene 54 may be supplied to the alkylation unit 56. Therefore, the alkylation effluent 60 exiting the alkylation unit 56 may contain alkylbenzene and unreacted benzene. Further, the alkylation effluent 60 may also include some unreacted paraffins. In FIG. 2, the alkylation effluent 60 is passed to a benzene separation unit 62, such as a fractionation column, for separating the unreacted benzene from the alkylation effluent 60. This unreacted benzene may exit the benzene separation unit 62 in a benzene recycle stream 64 that is delivered back into the alkylation unit 56 to reduce the volume of fresh benzene needed in stream 54.

As shown, a benzene-stripped stream 66 exits the benzene separation unit 62 and enters a paraffinic separation unit 68, such as a fractionation column. In the paraffinic separation unit 68, unreacted paraffins may be removed from the benzene-stripped stream 66 in a recycle paraffin stream 70, and may be routed to and mixed with the first portion of paraffins 24 before dehydrogenation as described above, or may optionally be directed to the second portion 26 for purification of product paraffins.

Further, an alkylbenzene stream 72 that is separated by the paraffinic separation unit 68 may be fed to an alkylate separation unit 74. The alkylate separation unit 74, which may be, for example, a multi-column fractionation system, separates a heavy alkylate bottoms stream 76 from the alkylbenzene stream 72.

After the post-alkylation separation processes, the alkylbenzene product 12, which contains some portion derived from waste plastic feedstock, may be isolated and exit the subsystem 10. It is noted that such separation processes are not necessary in all cases in order to isolate the alkylbenzene product 12. For instance, the alkylbenzene product 12 may be desired to have a wide range of carbon chain lengths and not require any fractionation to eliminate carbon chains longer than desired, e.g., heavies or carbon chains shorter than desired, e.g., lights. Further, the feed 114 may be of sufficient quality that no fractionation is necessary for the desired chain length range.

In FIG. 2, to produce olefins, a stream 53, which may include all or a portion of stream 52, may be directed to a separator 57 for separating the unconverted paraffins from the olefins. The separator 57 may be an Olex ® separator, available from UOP LLC. The Olex ® process involves the selective adsorption of a desired component (i.e., olefins) from a liquid-phase mixture by continuous contacting with a fixed bed of adsorbent. Alternatively, the separator 57 may be a direct sulfonation separator, which makes olefin sulfonate surfactants (containing some fraction that is derived from waste plastic feedstock) directly. The separated, unconverted paraffins may optionally be directed back to the second paraffin portion 26 for purification (stream 73) and/or back to the first paraffin portion 24 for dehydrogenation for conversion to olefins (stream 71). In FIG. 2, an olefin stream 61 may exit the separator 57 and may be fed to a separator 63. The separator 63 may be a multi-stage fractionation unit, distillation system, or similar known apparatus. The separator 63 may provide a means to separate the olefins into various desirable fractions. For example, as shown in FIG. 2, a first portion of olefins 65 and a second portion of olefins 67 are illustrated, although any number of olefin portions may be provided, depending on how many olefin fractions are desired. The first portion of olefins 65 may have carbon chain lengths of C10 to C14. Alternatively, the first portion of olefins 65 may have carbon chain lengths having a lower limit of $C_L$, where L is an integer from four (4) to thirty-one (31), and an upper limit of $C_U$, where U is an integer from five (5) to thirty-two (32). The second portion of olefins 67 may have carbon chains shorter than, longer than, or a combination of shorter and longer than, the chains of the first portion of olefins 65. The first portion of olefins 65 may include olefins with $C_{10}$ to $C_{14}$ chains and the second portion of olefins 67 may include olefins with $C_{18}$ to $C_{20}$ chains. Alternatively, the first portion of olefins 65 may include olefins with $C_{10}$ to $C_{13}$ chains and the second portion of olefins 67 may include olefins with $C_{14}$ to $C_{18}$ chains. Alternatively, the first portion of olefins 65 and/or the second portion of olefins 67 may include 2-carbon-cut olefins, such as $C_{14}$ to $C_{15}$. Subsequent to separation, the purified olefins portions 65 and 67 are removed from the subsystem 10 as the olefin product. The olefin products 65 and 67 may be used directly to produce oxo alcohols by known hydroformylation processes or fractionated further into 2- or 3-carbon-cuts prior to hydroformylation.

Figure 3:
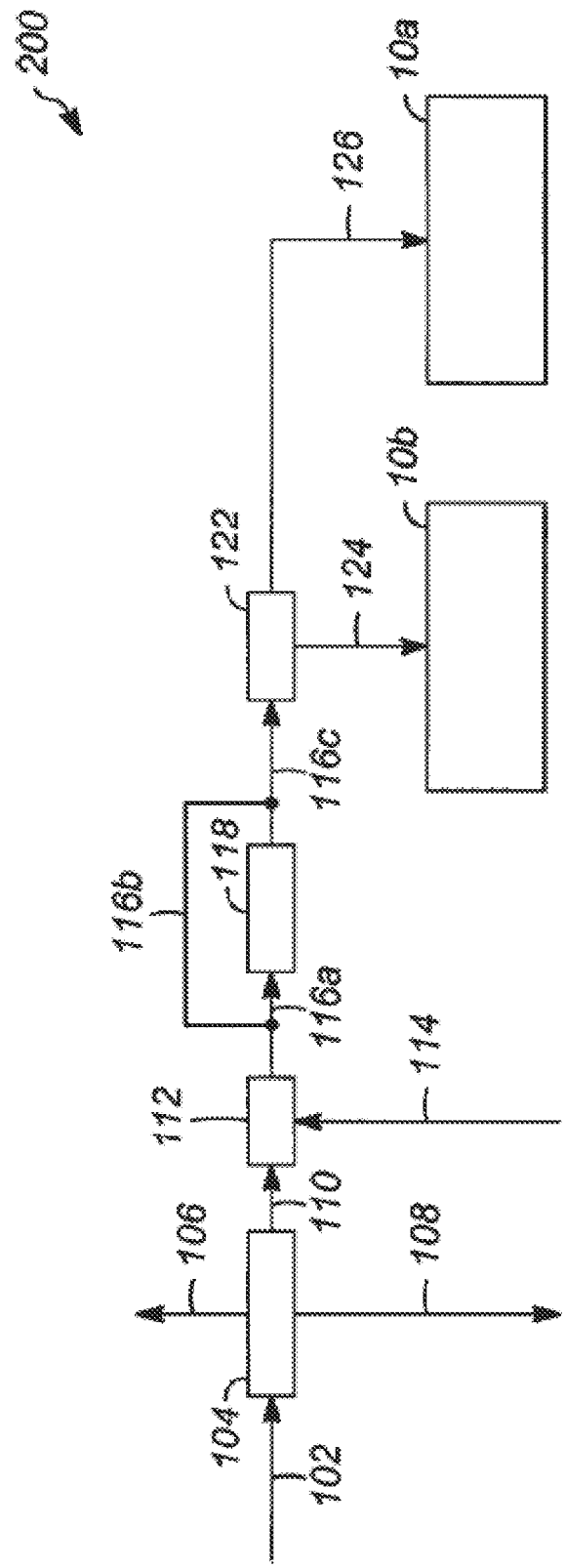
FIG. 3 schematically illustrates another system utilizing a process for producing alkylbenzenes, paraffins, and/or olefins from waste plastic feedstock and kerosene.

FIG. 3 depicts a system 200 using another example of a process for producing a alkylbenzene, paraffin, or olefin from waste plastic feedstock and kerosene and/or another source(s) of hydrocarbons as disclosed herein,. In FIG. 3, the heavy paraffins stream 124 is not directed out of the system 200 for optional use in other processes, as in FIG. 1, but rather is directed to a second subsystem 10b (stream 126 being directed to a first subsystem 10a) for the production of alkylbenzenes, paraffins, and/or olefins that are heavier than the heart cut. Subsystems 10a and 10b operate in the same manner as described above with regard to subsystem 10. For example, subsystems 10a and 10b may be separate systems for the simultaneous processing of the heart cut and the heavier paraffins, respectively. Alternatively, subsystems 10a and 10b may be the same system, where the heart cut and heavier paraffins are processed at different times.

Figure 4:
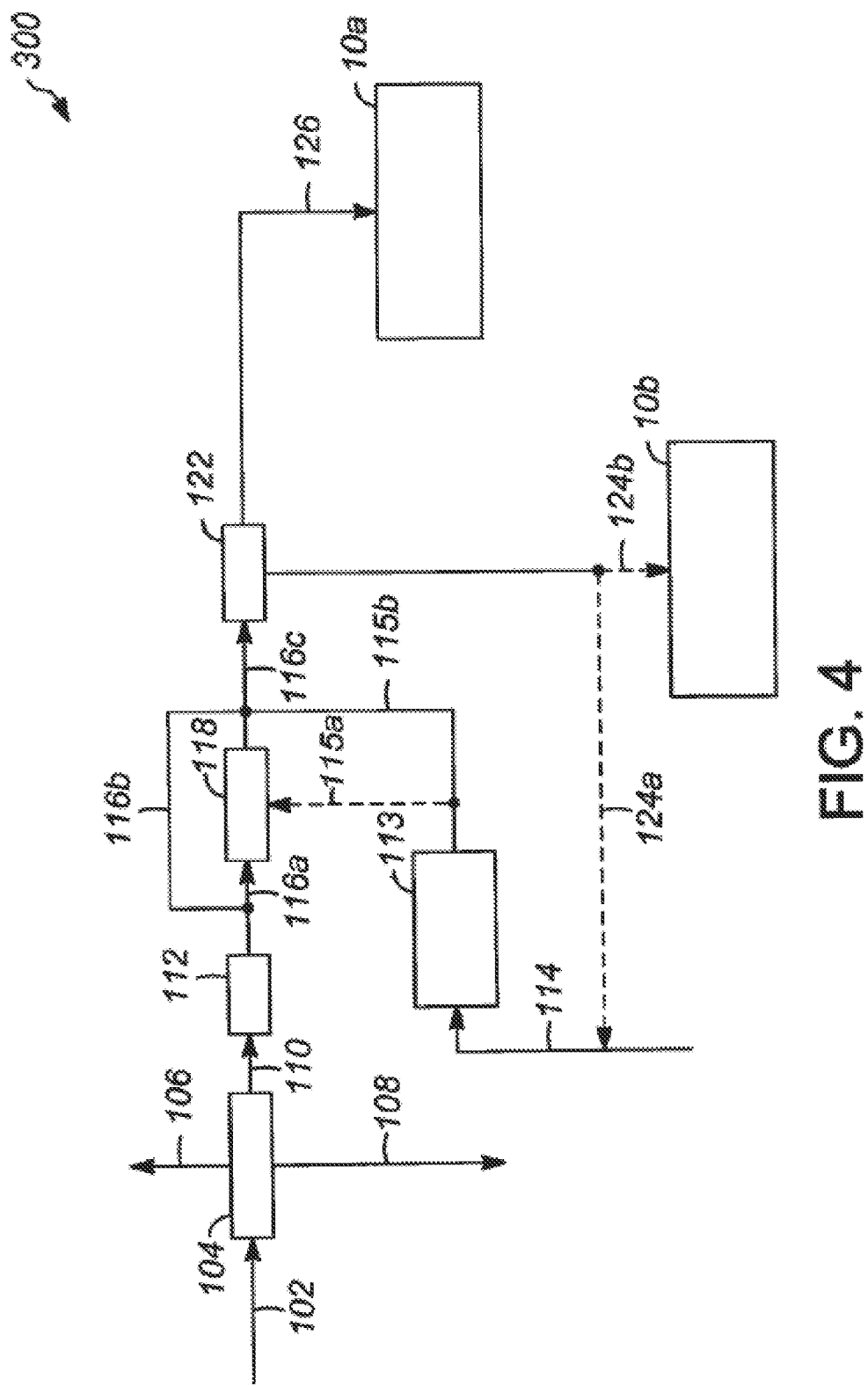
FIG. 4 schematically illustrates another system utilizing a process for producing alkylbenzenes, paraffins, and/or olefins from waste plastic feedstock and kerosene.

FIG. 4 depicts a system 300 using yet another example of a process for producing a alkylbenzene, paraffin, or olefin from waste plastic feedstock and kerosene and/or another source(s) of hydrocarbons as disclosed herein,. In FIG. 4, the waste plastic feedstock feed stream 114 may be hydrotreated (to form paraffins) in a hydrotreatment apparatus 113 prior to being combined with the paraffins from the kerosene feed 102. As such, the KHT 112 need not be configured for extensive hydrogenation, and a catalyst used therein may be selected solely for denitrification and desulfurization purposes. For example, a stream 115a of paraffins may exit the hydrotreatment apparatus 113 and feed into the separator 118, to separate branched and aromatic compounds. Alternatively, if such separation is not performed, a stream 115b of paraffins may be combined with the paraffins derived from the kerosene and/or another source(s) of hydrocarbons downstream of the separator 118. In this example, the heavy paraffins may either be removed from system 300 as discussed above with regard to FIG. 1 (stream 124a), further processed into alkylbenzenes, paraffins, and/or olefins (10b), as discussed above with regard to FIG. 3.

Figure 5:
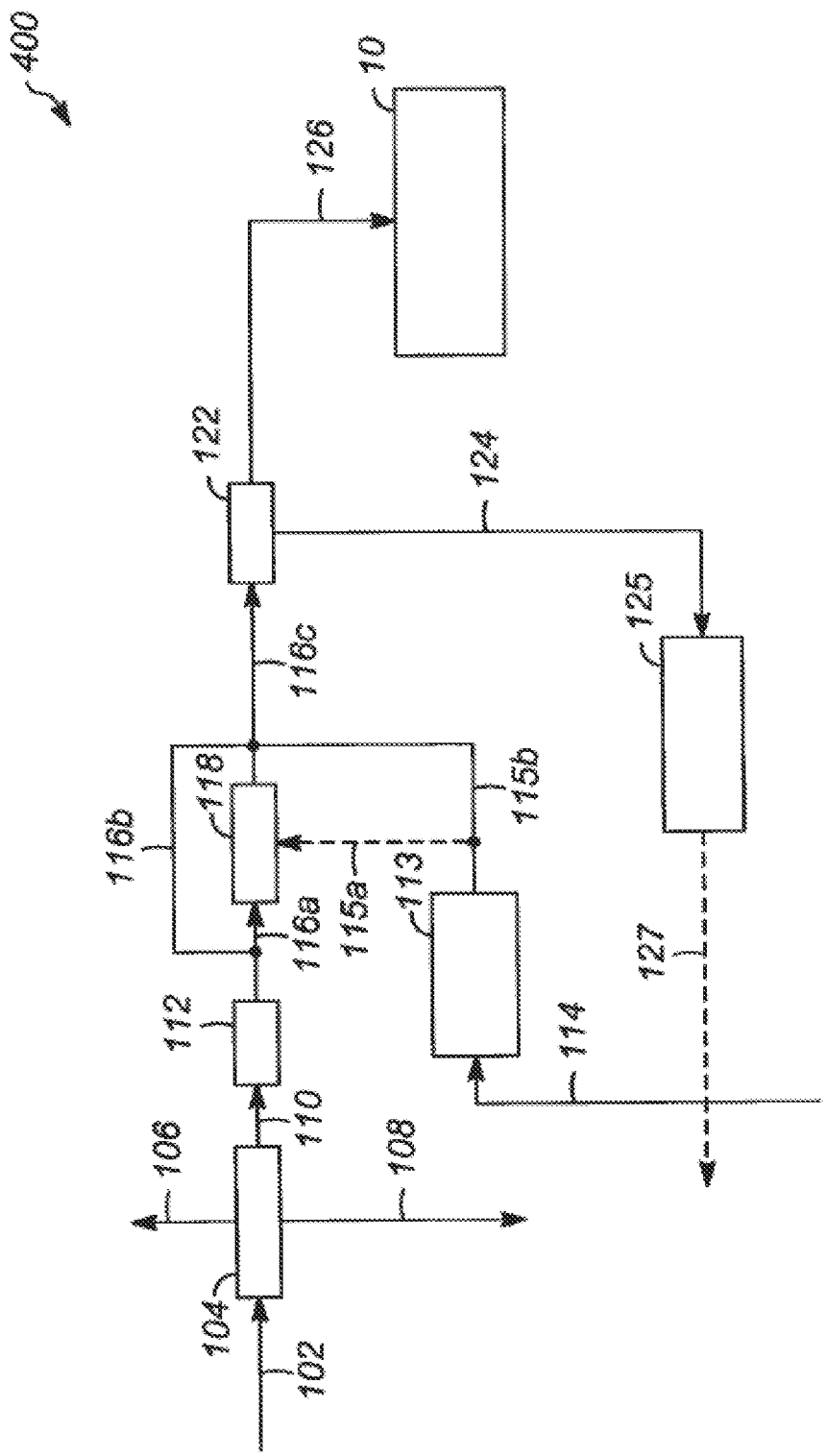
FIG. 5 schematically illustrates another system utilizing a process for producing alkylbenzenes, paraffins, and/or olefins from waste plastic feedstock and kerosene FIG. 6 schematically illustrates a system utilizing a process for producing alkylbenzenes, paraffins, and/or olefins from waste plastic feedstock alone.

FIG. 5 depicts a system 400 using still another example of a process for producing a alkylbenzene, paraffin, or olefin from waste plastic feedstock and kerosene and/or another source(s) of hydrocarbons. In FIG. 5, a heavy paraffin stream 124 is directed to an isomerization reactor 125. The isomerization reactor 125 is provided to convert the heavy paraffins stream 124 into a stream of branched paraffins and other compounds 127, which may have other industrial uses, such as fuel and/or for making branched oxo alcohols.

As noted above, FIG. 6 illustrates an example of a system utilizing a process for producing alkylbenzenes, paraffins, and/or olefins from waste plastic feedstock alone. In contrast to FIG. 1, in FIG. 6 feed 102, the kerosene feed, and unit 104 are eliminated. Only feed 114, the waste plastic feed, is fed into the hydrotreater 112. In FIG. 6, the hydrotreater 112 treats the feed 114 to reduce the olefin content and to reduce any impurities that may be present in the feed 114 in order to produce paraffin. The hydrotreater 112 employs a catalyst that is suitable for hydrogenation, deoxygenation and denitrification/desulfurization or a mix of catalysts that each accomplish one or more of hydrogenation, deoxygenation, denitrification, and desulfurization. A suitable KHT 112 apparatus for use in embodiments of the present disclosure is sold by UOP LLC.

A treated stream of paraffins 116a exiting the hydrotreater 112 may be fed to a separator 118 to separate linear paraffins from branched or cyclic paraffins that may be included in the stream 116a. A suitable separator for this purpose is a separator that operates using the UOP LLC Molex® process, which is a liquid-state separation of normal paraffins from branched and cyclic components using UOP LLC Sorbex® technology. Other separators known in the art are suitable for use herein as well.

Depending on the composition of the waste plastic feed 114 (e.g., waste plastic feedstock derived from pure polyethylene), separation of linear paraffins from branched and cyclic components may not be necessary, and a hydrotreated stream of paraffins 116b from the hydrotreater 112 may be directed downstream for further processing.

A linear paraffin stream 116c exiting the separator 118 or the treated stream of paraffins 116b may be fed to a fractionator 122. The waste plastic feed 114 may include hydrocarbons that are heavier and/or lighter than the heart cut range, and as such the fractionator 122 may be provided to fractionate hydrocarbons that are heavier and/or lighter than the desired heart cut range in the waste plastic stream. Hydrocarbons that are $C_{14}$ and heavier may removed from system 100 in a heavy paraffins stream 124 and may be used in other processes. Hydrocarbons anywhere in the range from $C_{15}$ - $C_{18}$ and heavier may be removed from system 100 in the heavy paraffins stream 124. The paraffins in the desired heart cut range exit the fractionator 122 in a stream 126 for further processing into alkylbenzene, paraffin, and/or olefin in subsystem 10 (FIG. 2). Paraffins produced by the system of FIG. 6 and fed to subsystem 10, however, are derived from 100% waste plastic feedstock. Previous disclosed details about FIG. 2 and subsystem 10 may apply downstream of FIG. 6 as well to produce, for example, alkylbenzene, where the non-aromatic portion of the alkyl benzene is derived entirely from waste plastic.

Figure 7:
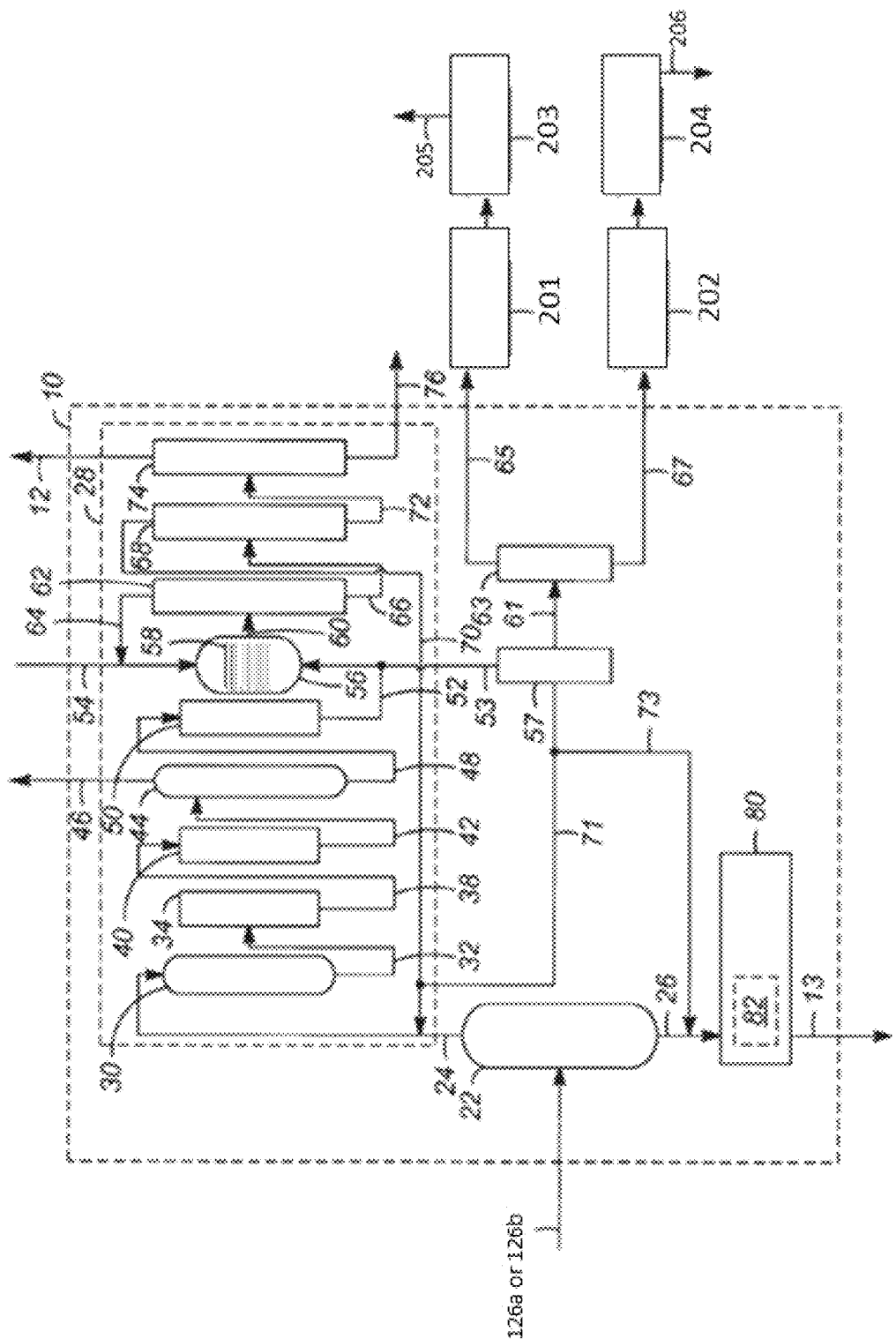
FIG. 7 schematically illustrates a system utilizing a process for producing oxo alcohols, paraffins, and/or olefins from waste plastic feedstock and kerosene.

FIG. 7 schematically illustrates an example of a system utilizing a process for producing linear and/or branched oxo alcohols, linear and/or branched paraffins, and/or linear and/or branched olefins from waste plastic feedstock and kerosene and/or another source(s) of hydrocarbons. The steps prior to entering subsystem 10 in FIG. 7 are diagrammed in FIG. 1 and discussed above. In FIG. 7, in contrast to FIG. 2, instead of feeding a stream of monoolefins 52 and a stream of benzene 54 into an alkylation unit 56, a stream 53, which may include all or a portion of stream 52, is directed to a separator 57 for separating unconverted paraffins from the olefins. The separator 57 may be an Olex® separator, available from UOP LLC. The Olex® process involves the selective adsorption of a desired component (i.e., olefins) from a liquid-phase mixture by continuous contacting with a fixed bed of adsorbent. The separator 57 may be a direct sulfonation separator. The separated, unconverted paraffins may optionally be directed back to the second paraffin portion 26 for purification (stream 73) and/or back to the first paraffin portion 24 for dehydrogenation for conversion to olefins (stream 71). In FIG. 7, an olefins stream 61 may exit the separator 57 and may be fed to a separator 63. The separator 63 may be a multi-stage fractionation unit, distillation system, or similar known apparatus. The separator 63 may provide a means to separate the olefins into various desirable fractions. For example, as shown in FIG. 7, a first portion of olefins 65 and a second portion of olefins 67 are illustrated, although any number of olefin portions may be provided, depending on how many olefin fractions are desired. The first portion of olefins 65 may have carbon chain lengths of C10 to $C_{14}$. The first portion of olefins 65 may have carbon chain lengths having a lower limit of $C_L$, where L is an integer from four (4) to thirty-one (31), and an upper limit of $C_u$, where U is an integer from five (5) to thirty-two (32).

The second portion of olefins 67 may have carbon chains shorter than, longer than, or a combination of shorter and longer than, the chains of the first portion of olefins 65. The first portion of olefins 65 may include olefins with $C_{10}$ to $C_{14}$ chains and the second portion of olefins 67 may include olefins with $C_{18}$ to $C_{20}$ chains. Subsequent to separation, the purified olefins portions 65 and 67 are removed from the subsystem 10 as the olefin product. Alternatively, the separator 63 produces two-carbon-cut olefins, such as $C_{14}$-$C_{15}$, $C_{16}$-$C_{17}$ or $C_{17}$-$C_{18}$, or any combination of the above. Alternatively, when the first portion of olefins 65 includes $C_{10}$-$C_{14}$ olefins, this portion may be further fractionated to produce $C_{11}$-$C_{12}$, $C_{13}$-$C_{14}$, or both, depending on the separator configuration and the need for further processing. These olefin portions 65, 67 may be fed into oxo units 201, 202 to produce oxo alcohols, using known hydroformylation processes. Suitable oxo catalysts for hydroformylation include rhodium and/or cobalt catalysts, which may be modified or unmodified. The two streams of oxo alcohols may then be fed into a separator 203, 204 to remove hydroformylation catalyst from the stream and produce purified streams of oxo alcohols 205, 206.

Figure 8:
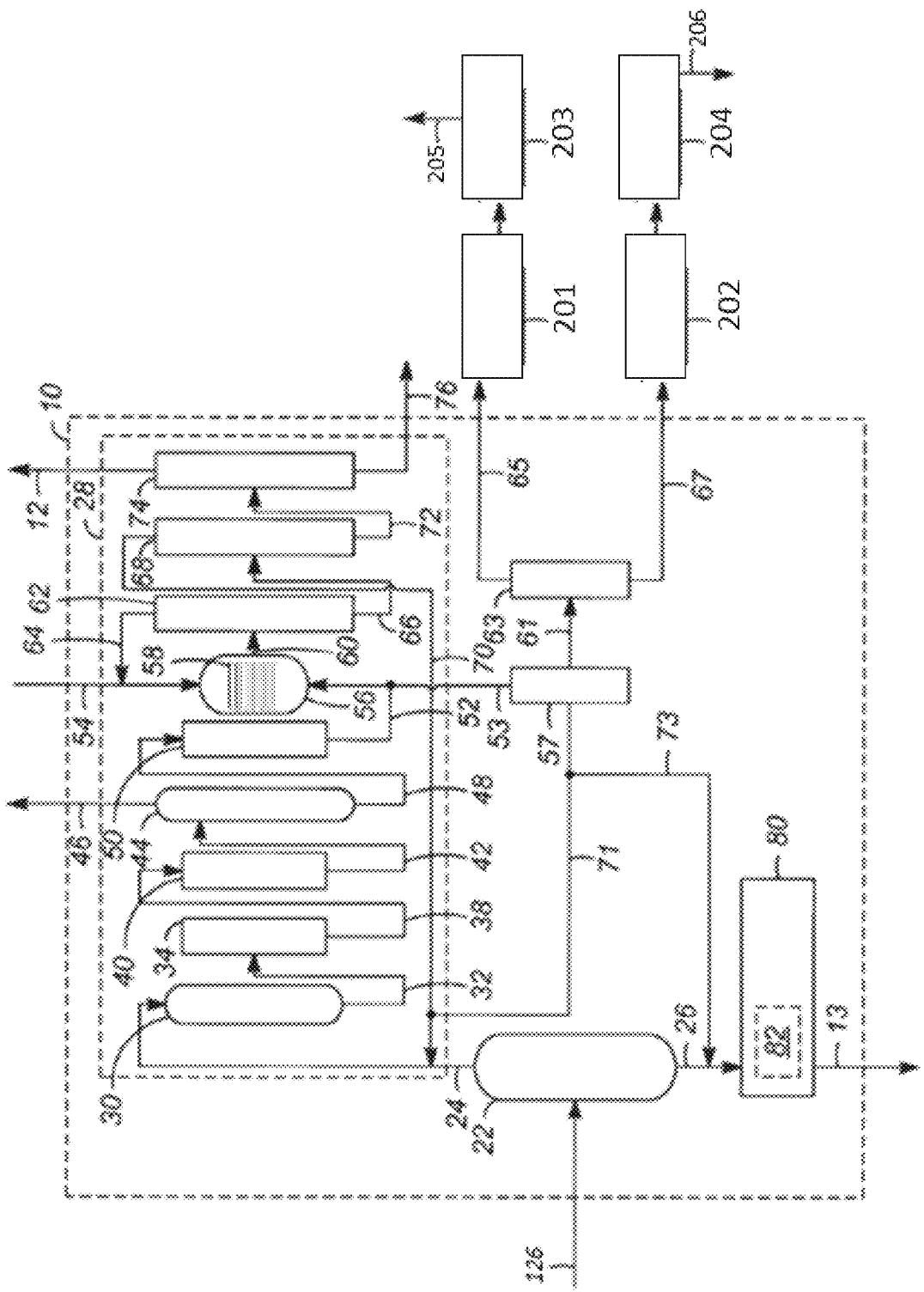
FIG. 8 schematically illustrates a system utilizing a process for producing oxo alcohols, paraffins, and/or olefins from only waste plastic feedstock.

FIG. 8 schematically illustrates an example of a system utilizing a process for producing linear or branched oxo alcohols, linear or branched paraffins, and/or linear or branched olefins from waste plastic feedstock alone (FIG. 8 represents a combination of FIG. 6 and FIG. 7). FIG. 6 illustrates a process of producing paraffin from waste plastic feedstock alone. FIG. 6 coupled with FIG. 7, which illustrates a system 10 utilizing a process for producing linear and/or branched oxo alcohols, linear and/or branched paraffins, and/or linear and/or branched olefins, illustrates a process for producing a linear or branched oxo alcohol that is derived only from plastic waste feedstock and, for example, syngas.

In another example, which is not illustrated, linear and/or branched paraffin, produced according to any of the above-described processes, may be converted to a linear and/or branched paraffin sulfonate, using known sulfoxidation processes, and may be included in a detergent formulation.

In another example, which is not illustrated, linear and/or branched olefin may be sulfonated, using known processes (e.g., $SO_3$, oleum, or other sulfonating agents) to produce a linear and/or branched olefin sulfonate surfactant, which may also be used in detergent formulations.

In another example, which is not illustrated, the linear and/or branched oxo alcohol product shown in FIG. 7 or FIG. 8, is converted to a linear and/or branched tertiary amine, using known reaction conditions (e.g., using dimethyl amine in the presence of a catalyst under low hydrogen conditions). The linear and/or branched tertiary amine may be converted (under known conditions via oxidation) to a linear and/or branched amine oxide.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Detergent Compositions

The detergent compositions described herein may comprise a surfactant in an amount sufficient to provide desired cleaning properties. The detergent compositions may comprise from about 1% to about 75%, by weight of the composition, of a surfactant. The detergent compositions may comprise from about 2% to about 35%, by weight of the composition, of a surfactant. The detergent compositions may comprise from about 5% to about 10%, by weight of the composition, of a surfactant.

The detergent compositions may comprise a plastic waste-derived surfactant content of at least about 50%, or at least about 70%, or at least about 80%, or at least about 90% (meaning that at least about 50%, or at least about 70%, or at least about 80%, or at least about 90% of the total surfactant in the detergent composition is plastic waste-derived).

In particular, the detergent compositions may comprise a plastic waste-derived surfactant produced according to the methods described herein. The detergent compositions may comprise a plastic waste-derived sulfonated linear alkylbenzene, a plastic waste-derived sulfated detergent alcohol, and/or a plastic waste-derived paraffin sulfonate produced according to the method(s) described herein. The detergent compositions may comprise a plastic waste-derived surfactant produced by the method(s) disclosed herein in combination with natural alcohol sulfates and/or natural alcohol ethoxylated sulfates, such as those derived from the reduction of methyl esters to fatty alcohols.

The detergent compositions may comprise a plastic waste-derived surfactant produced by the method(s) disclosed herein in combination with a conventional kerosene-based surfactant. The conventional kerosene-based surfactant may be selected from the group consisting of anionic surfactants, nonionic surfactants, cationic surfactants, zwitterionic surfactants, amphoteric surfactants, ampholytic surfactants, and mixtures thereof.

Combinations of Surfactants

The detergent compositions may comprise a plastic waste-derived anionic surfactant and a plastic waste-derived or conventional kerosene-based nonionic surfactant, e.g., C12-C18 alkyl ethoxylate. The detergent compositions may comprise a plastic waste-derived alkyl benzene sulfonates (LAS) and another, optionally plastic waste-derived, anionic surfactant, e.g., C10-C18 alkyl alkoxy sulfates (AExS), where x is from 1-30, where the plastic waste-derived surfactants are produced according to the methods described herein. The detergent compositions may comprise a plastic waste-derived anionic surfactant and a cationic surfactant, for example, dimethyl hydroxyethyl lauryl ammonium chloride. The detergent compositions may comprise a plastic waste-derived anionic surfactant and a zwitterionic surfactant, for example, $C_{12}$-$C_{14}$ dimethyl amine oxide.

Adjunct Cleaning Additives

The detergent compositions of the invention may also contain adjunct cleaning additives. Suitable adjunct cleaning additives include builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes.

Processes of Making Detergent Compositions

The detergent compositions of the present invention can be formulated into any suitable form and prepared by any process chosen by the formulator.

Methods of Use

The present disclosure includes methods for cleaning soiled material. As will be appreciated by one skilled in the art, the detergent compositions of the present invention are suited for use in laundry pretreatment applications, laundry cleaning applications, and home care applications.

Such methods include, but are not limited to, the steps of contacting detergent compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the detergent compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry detergent composition in accord with the invention. An "effective amount" of the detergent composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 30:1. The compositions may be employed at concentrations of from about 500 ppm to about 15,000 ppm in solution. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The detergent compositions herein may be used for laundering of fabrics at reduced wash temperatures. These methods of laundering fabric comprise the steps of delivering a laundry detergent composition to water to form a wash liquor and adding a laundering fabric to said wash liquor, wherein the wash liquor has a temperature of from about 0° C. to about 20° C., or from about 0° C. to about 15° C., or from about 0° C. to about 9° C. The fabric may be contacted to the water prior to, or after, or simultaneously with, contacting the laundry detergent composition with water.

Another method includes contacting a nonwoven substrate, which is impregnated with the detergent composition, with a soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SONTARA® by DuPont and POLYWEB® by James River Corp.

Hand washing/soak methods, and combined handwashing with semi-automatic washing machines, are also included.

Machine Dishwashing Methods

Methods for machine-dishwashing or hand dishwashing soiled dishes, tableware, silverware, or other kitchenware, are included. One method for machine dishwashing comprises treating soiled dishes, tableware, silverware, or other kitchenware with an aqueous liquid having dissolved or dispensed therein an effective amount of a machine dishwashing composition in accord with the invention. By an effective amount of the machine dishwashing composition it is meant from about 8 g to about 60 g of product dissolved or dispersed in a wash solution of volume from about 3 L to about 10 L.

One method for hand dishwashing comprises dissolution of the detergent composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the detergent composition onto soiled dishes, tableware, silverware, or other kitchenware, then hand scrubbing, wiping, or rinsing the soiled dishes, tableware, silverware, or other kitchenware. In some examples, an effective amount of detergent composition for hand dishwashing is from about 0.5 ml. to about 20 ml. diluted in water.

Packaging for the Compositions

The detergent compositions described herein can be packaged in any suitable container including those constructed from paper, cardboard, plastic materials, and any suitable laminates.

Multi-Compartment Pouch Additive

The detergent compositions described herein may also be packaged as a multi-compartment detergent composition.

ANALYSIS METHODS AND EXAMPLES

GC Sample Prep:

In order to identify the various products of the process, derivatization is performed. All data reported herein on the Agilent Technologies Gas Chromatograph 7890A instrument are in area %.

Derivatized samples are prepared by drying a 1 ml sample of the reactor effluent over $MgSO_4$, filtering, and adding 20 µl of resultant to a vial followed by 1.5 ml of 14% BF3 in MeOH and heating to 65° C. for 30 minutes. 1.5 ml of water is then added followed by 2.0 ml of hexane. This is then shaken and the organic layer is allowed to separate. Once separated, the top organic layer is dried through a $MgSO_4$ plug into a GC vial. The resultant sample is analyzed by GC using the following:

Agilent Technologies Gas Chromatograph 7890A equipped with a split/splitless injector and FID;

J&W Scientific capillary column DB-1HT, 30 meter, 0.25 mm id, 0.1 µm film thickness cat# 1221131;

EMD Chemicals HPLC grade Chloroform, cat# EM-CX1058-1 or equivalent;

2 ml GC autosampler vials with screw tops, or equivalent.

GC Parameters:

Carrier Gas: Helium

Column Head Pressure: 18.5 psi

Flows: Column Flow @ 1.6 ml/min.

Split Vent @ 19.2 ml/min.

Septum Purge @ 3 ml/min.

Injection: Agilent Technologies 7693 Series Autosampler, 10 ul syringe, 1 ul injection Injector Temperature: 275° C.

Detector Temperature: 340° C.

Oven Temperature Program: initial 70° C. hold 1 min.

rate 10° C./min.

final 320° C. hold 5 min.

Another procedure to analyze for impurities in the paraffin is 2D GCMS. This system is well known in the analytical literature as providing the best way to separate complex compositions and to identify by mass spectroscopy the types of materials separated.

2D GCMS Analysis Procedure:

2D-GC/FID—Relatively Quantitative Comparison

Equipment:

Leco Comprehensive 2-dimensional Gas Chromatograph

Agilent 7890 GC System (Leco modified) w/split/splitless injector & flame ionization detector (FID)

Leco Secondary oven

Leco LN2 modulator and controller

CTC Combi-PAL Autosampler (or equivalent)

Columns:

Supelco Gamma DEX 120 (30×0.25 mm ID×0.25 um df)

Deactivated transfer line Restek 'Siltek' (0.66 m×0.25 mm ID)

Varian VF-5ms (2m×0.15 mm ID×0.15 um df)

In the following configuration:

| # | Type | Location | Length (m) | Int. Diameter (µ) | Max Temp (° C.) | Film Thickness (µ) | Phase |
|---|---|---|---|---|---|---|---|
| 1 | Inlet | Front | | | | | |
| 2 | Capillary | GC Oven | 30.000 | 250.00 | 235.0 | 0.25 | G-DEX 120 |
| 3 | Capillary | Modulator | 0.660 | 250.00 | 350.0 | 0.00 | Deactivated FS |
| 4 | Capillary | Secondary Oven | 1.770 | 150.00 | 360.0 | 0.15 | VF-5ms |
| 5 | Capillary | Detector or MS Transfer Line | 0.330 | 150.00 | 360.0 | 0.15 | VF-5ms |

Sample Preparation:

Dilute sample 100:1 in dichlormethane (DCM) as follows:

Pipette 10 uL of paraffin or kerosene sample into 2mL GC vial

Pipette 990 uL DCM into same GC vial

Cap with septa seal and mix (vortex mixer) 20 seconds.

Instrument Parameters:

Carrier Gas: Helium @ 1.1mL/min (constant flow mode)

Injection: 1 uL Split 50:1 @200° C.

Primary Oven:

Initial 35° C. hold 2 min.

Ramp 1—1° C./min to 200° C.

Ramp 2—5° C./min to 220° C.

Secondary Oven: +10° C. offset tracking primary oven

Modulator Temp: +25° C. offset tracking primary oven

Modulator Program:

Entire run—18.5 second modulation period

Hot pulse time—8.75 seconds

Cool time between stages 0.5 seconds

Detector: (FID)

Temp. 300° C.

Data collection rate: 200Hz

Makeup 25 mL/min Nitrogen (Makeup +column)

Hydrogen: 40 mL/min

Air: 450 mL/min

2D-GC/TOFMS—Qualitative Composition

Equipment:

Leco Pegasus 4D—Comprehensive 2-D GC+Time-of-Flight Mass Spectrometer

Leco Comprehensive 2-dimensional Gas Chromatograph

Agilent 7890 GC System (Leco modified) w/split/splitless injector & flame ionization detector (FID)

Leco Secondary oven

Leco LN2 modulator and controller

CTC Combi-PAL Autosampler (or equivalent)

Columns:

Supelco Gamma DEX 120 (30m ×0.25mm ID×0.25um df)

Deactivated transfer line 'Restek Siltek' (0.4m×0.25mm ID)

Restek rxi-XLB (2.1m×0.18mm ID×0.18um df)

In the following configuration:

| # | Type | Location | Length (m) | Int. Diameter (μ) | Max Temp (° C.) | Film Thickness (μ) | Phase |
|---|---|---|---|---|---|---|---|
| 1 | Inlet | Front | | | | | |
| 2 | Capillary | GC Oven | 30.000 | 250.00 | 250.0 | 0.25 | G-DEX 120 |
| 3 | Capillary | Modulator | 0.400 | 250.00 | 360.0 | 0.00 | Deactivated FS |
| 4 | Capillary | Secondary Oven | 2.000 | 180.00 | 360.0 | 0.18 | rxi-BXL |
| 5 | Capillary | Detector or MS Transfer Line | 0.100 | 180.00 | 360.0 | 0.18 | rxi-XLB |
| 6* | Detector | TOF | | | | | |

Sample Preparation:

Dilute sample 100:1 in dichlormethane (DCM) eg. as follows:

Pipette 10 uL of paraffin or kerosene sample into 2 mL GC vial

Pipette 990 uL DCM into same GC vial

Cap with septa seal and mix (vortex mixer) 20 seconds

Instrument Parameters:

Carrier Gas: Helium @ 1.1 mL/min (constant flow mode)

Injection: 1 uL Split 50:1 @200° C.

Primary Oven:

Initial 35° C. hold 2 min.

Ramp 1—1° C./min to 200° C.

Ramp 2—5° C./min to 220° C.

Secondary Oven: +10° C. offset tracking primary oven

Modulator Temp: +25° C. offset tracking primary oven

Modulator Program:

Entire run—18.5 second modulation period

Hot pulse time—8.75 seconds

Cool time between stages 0.5 seconds

Detector: (TOF-MS)

Tranfer line Temperature: 250° C.

Data collection rate: 200 spectra/second

Electron Energy: −70V

Mass Range 45-450 m/z

Solvent Delay: 150 seconds

Source Temperature: 210° C.

HT-GC/FID—High Temp Fast GC for High Boilers (FFE & Residual Triglyceride)

Equipment:

Agilent 7890 GC System w/split/splitless injector & flame ionization detector (FID)

Agilent 7693 Autosampler (or equivalent)

Columns:

Agilent J&W DB1-HT (5m×0.25mm ID×0.1um df—cut from 30m Column # 122-1131)

Sample Preparation:

Dilute sample 100:1 in dichlormethane (DCM) eg. as follows:

Pipette 10 uL of paraffin or kerosene sample into 2mL GC vial

Pipette 990uL DCM into same GC vial

Cap with septa seal and mix (vortex mixer) 20 seconds

Instrument Parameters:

Carrier Gas: Helium @ 1.4 mL/min (constant flow mode)

Injection: 1uL Pulsed Split 25:1 @ 325° C.

Pressure Pulse: 10psi until 0.15min.

Oven Program:

Initial 40° C. hold 0.5 min.

Ramp 1—40° C./min to 380° C. hold 3 min.

Detector: (FID)

Temp. 380° C.

Data collection rate: 50Hz

Makeup 25 mL/min Helium o Hydrogen: 40 mL/min

Air: 450 mL/min

DETERGENT FORMULATION EXAMPLES

Example 1

Heavy Duty Liquid Laundry Detergent Compositions

| Ingredient | Liquid Detergent A (wt %) | Liquid Detergent B (wt %) | Liquid Detergent C (wt %) | Liquid Detergent D (wt %) | Liquid Detergent (wt %) |
|---|---|---|---|---|---|
| Plastic waste-derived or conventional kerosene-based AES[10] | 1-12 | 0 | 1-12 | 1-12 | 1-12 |
| Plastic waste-derived or conventional kerosene-based LAS[11] | 5-20 | 15-30 | 1-5 | 10-20 | 1-5 |
| Sodium formate | 2.66 | 2.66 | 2.66 | 2.66 | 0.11 |
| Calcium formate | — | — | — | — | 0.097 |
| Sodium hydroxide | 0.21 | 0.21 | 0.21 | 0.21 | 0.68 |
| Monoethanolamine (MEA) | 1.65 | 1.65 | 1.65 | 1.65 | 2.80 |
| Diethylene glycol (DEG) | 4.10 | 4.10 | 4.10 | 4.10 | 1.23 |
| Propylene glycol | — | — | — | — | 8.39 |
| Plastic waste-derived or conventional kerosene-based AE9[2] | 0.40 | 0.40 | 0.40 | 0.40 | — |
| C16AE7 | 3.15 | 3.15 | 3.15 | 3.15 | — |
| NI 24-9[8] | — | — | — | — | 0.97 |
| Chelant[3] | 0.18 | 0.18 | 0.18 | 0.18 | 0.29 |
| Citric Acid | 1.70 | 1.70 | 1.70 | 1.70 | 2.83 |
| $C_{12-18}$ Fatty Acid | 1.47 | 1.47 | 1.47 | 1.47 | 1.09 |
| Borax | 1.19 | 1.19 | 1.19 | 1.19 | 2.00 |
| Ethanol | 1.44 | 1.44 | 1.44 | 1.44 | 1.47 |
| Ethoxylated Polyethyleneimine[1] | 1.35 | 1.35 | 1.35 | 1.35 | 1.85 |
| Amphiphilic alkoxylated grease cleaning polymer[7] | — | — | — | — | 0.940 |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | 0.40 | 0.40 | 0.40 | 0.40 | 1.40 |
| 1,2-Propanediol | 2.40 | 2.40 | 2.40 | 2.40 | — |
| Protease (54.5 mg active/g)[9] | 0.89 | 0.89 | 0.89 | 0.89 | 0.95 |
| Mannanase: Mannaway ® (25.6 mg active/g)[5] | 0.04 | 0.04 | 0.04 | 0.04 | — |
| Xyloglucanase: Whitezyme ® (20 mg active/g)[14] | — | — | — | — | 0.04 |
| Cellulase: Carezyme ™ (11.63 mg active/g)[14] | — | — | — | — | 0.10 |
| Amylase: Natalase ® (29 mg active/g)[5] | 0.14 | 0.14 | 0.14 | 0.14 | 0.34 |
| Fluorescent Whitening Agents[10] | 0.10 | 0.10 | 0.10 | 0.10 | 0.15 |
| Water, perfume, dyes & other components | | Balance | | | Balance |

[1] Polyethyleneimine (MW = 600) with 20 ethoxylate groups per —NH.
[2] AE9 is $C_{12-13}$ alcohol ethoxylate, with an average degree of ethoxylation of 9, made according the methods disclosed herein or via a conventional kerosene-based process.
[3] Suitable chelants are, for example, diethylenetetraamine pentaacetic acid (DTPA) supplied by Dow Chemical, Midland, Michigan, USA or Hydroxyethane di phosphonate (HEDP) supplied by Solutia, St Louis, Missouri, USA Bagsvaerd, Denmark
[4] Natalase ®, Mannaway ® are all products of Novozymes, Bagsvaerd, Denmark.
[5] Proteases may be supplied by Genencor International, Palo Alto, California, USA (e.g. Purafect Prime ®) or by Novozymes, Bagsvaerd, Denmark (e.g. Liquanase ®, Coronase ®).
[6] Suitable Fluorescent Whitening Agents are for example, Tinopal ® AMS, Tinopal ® CBS-X, Sulphonated zinc phthalocyanine Ciba Specialty Chemicals, Basel, Switzerland
[7] Amphiphilic alkoxylated grease cleaning polymer is a polyethyleneimine (MW = 600) with 24 ethoxylate groups per —NH and 16 propoxylate groups per —NH.
[8] Huntsman, Salt Lake City, Utah, USA.
[9] Novozymes A/S, Bagsvaerd, Denmark.
[10] AES is $C_{12-14}$ alkyl ethoxy (3) sulfate, $C_{14-15}$ alkyl ethoxy (2.5) sulfate, or $C_{12-15}$ alkyl ethoxy (1.8) sulfate made according the methods disclosed herein or via a conventional kerosene-based process.
[11] LAS is made according the methods disclosed herein or via a conventional kerosene-based process.

Example 2

Unit Dose Compositions—Unit dose laundry detergent formulations can comprise one or multiple compartments.

| Ingredient | (wt %) | (wt %) | (wt %) | (wt %) | (wt %) |
|---|---|---|---|---|---|
| Ethoxylated glycerine (EO$_{1-24}$) | 4 | 0 | 3 | 4 | 0 |
| 1,2 propanediol | 7 | 18.8 | 13.8 | 13.8 | 15.8 |
| Glycerine | 4 | 0 | 3.1 | 2.1 | 4.1 |
| Di Propylene Glycol | 4 | 0 | 0 | 0 | 0 |
| Sodium cumene sulphonate | 0 | 0 | 0 | 0 | 2.0 |
| Plastic waste-derived or conventional kerosene-based AES | 8 | 18 | 9.5 | 12.5 | 10 |
| Plastic waste-derived or conventional kerosene-based LAS | 5 | 18 | 9.5 | 14.5 | 7.5 |
| Plastic waste-derived or conventional kerosene-based Isalchem ® 156AS | 15 | 0 | 5 | 0 | 10 |
| Plastic waste-derived or conventional kerosene-based AE | 13 | 3 | 16 | 2 | 13 |
| Citric Acid | 1 | 0.6 | 0.6 | 1.56 | 0.6 |
| C$_{12-18}$ Fatty Acid | 4.5 | 10 | 4.5 | 14.8 | 4.5 |
| Enzymes | 1.0 | 1.7 | 1.7 | 2.0 | 1.7 |
| Ethoxylated Polyethylenimine | 1.4 | 1.4 | 4.0 | 6.0 | 4.0 |
| Chelant | 0.6 | 0.6 | 1.2 | 1.2 | 3.0 |
| PEG-PVAc Polymer | 4 | 2.5 | 4 | 2.5 | 1.5 |
| Fluorescent Brightener | 0.15 | 0.4 | 0.3 | 0.3 | 0.3 |
| Monoethanolamine | 9.8 | 8.0 | 8.0 | 8.0 | 9.8 |
| TIPA | 0 | 0 | 2.0 | 0 | 0 |
| Triethanolamine | 0 | 2.0 | 0 | 0 | 0 |
| Cyclohexyl dimethanol | 0 | 0 | 0 | 2.0 | 0 |
| Water | 12 | 10 | 10 | 10 | 10 |
| Structurant | 0.1 | 0.14 | 0.14 | 0.1 | 0.14 |
| Perfume | 0.2 | 1.9 | 1 | 1.9 | 1.9 |
| Hueing Agent | 0 | 0.1 | 0.001 | 0.0001 | 0 |
| Buffers | To pH 8.0 | | | | |
| Other Solvents (ethanol) | To 100% | | | | |

All enzyme levels are expressed as % enzyme raw material.

Raw Materials for Examples 2

AES is C$_{12-14}$ alkyl ethoxy (3) sulfate, C$_{14-15}$ alkyl ethoxy (2.5) sulfate, or C$_{12-15}$ alkyl ethoxy (1.8) sulfate made according the methods disclosed herein or via a conventional kerosene-based process.

Isalchem 156AS is an alcohol sulfate derived from the non-selective cobalt hydroformylation of an oxo alcohol, made according to the methods disclosed herein or via a conventional kerosene-based process.

AE is selected from C$_{12-13}$ with an average degree of ethoxylation of 6.5, C$_{11-16}$ with an average degree of ethoxylation of 7, C$_{12-14}$ with an average degree of ethoxylation of 7, C$_{14-15}$ with an average degree of ethoxylation of 7, or C$_{12-14}$ with an average degree of ethoxylation of 9, all made according the methods disclosed herein or via a conventional kerosene-based process.

PEG-PVAc polymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).

Ethoxylated Polyethylenimine is a 600 g/mol molecular weight polyethylenimine core with 20 ethoxylate groups per —NH. Available from BASF (Ludwigshafen, Germany).

Amylases (Natalase®, Stainzyme®, Stainzyme Plus®) may be supplied by Novozymes, Bagsvaerd, Denmark.

Savinase®, Lipex®, Celluclean™, Mannaway®, Pectawash®, and Whitezyme® are all products of Novozymes, Bagsvaerd, Denmark.

Proteases may be supplied by Genencor International, Palo Alto, California, USA (e.g. Purafect Prime®) or by Novozymes, Bagsvaerd, Denmark (e.g. Liquanase®, Coronase®).

Suitable Fluorescent Whitening Agents are for example, Tinopal® TAS, Tinopal® AMS, Tinopal® CBS-X.

Chelant is selected from, diethylenetetraamine pentaacetic acid (DTPA) supplied by Dow Chemical, Midland, Michigan, USA, hydroxyethane di phosphonate (HEDP) supplied by Solutia, St Louis, Missouri, USA; Ethylenediamine-N,N'-disuccinic acid, (S,S) isomer (EDDS) supplied by Octel, Ellesmere Port, UK, Diethylenetriamine penta methylene phosphonic acid (DTPMP) supplied by Thermphos, or 1,2-dihydroxybenzene-3,5-disulfonic acid supplied by Future Fuels Batesville, Arkansas, USA Hueing agent is Direct Violet 9 or Direct Violet 99, supplied by BASF, Ludwigshafen, Germany.

Soil release agent is Repel-o-tex® PF, supplied by Rhodia, Paris, France.

Structurant is hydrogenated castor oil (e.g., Thixin®).

What is claimed is:

1. A method for producing olefin from waste plastic feedstock and kerosene and/or another source(s) of hydrocarbons comprising the steps of:
   providing a first feed stream comprising kerosene and/or another source(s) of hydrocarbons;
   pre-fractionating the first feed stream by separating and removing both a light hydrocarbon stream comprising C$_8$ and lighter hydrocarbons, and a heavier hydrocarbon stream, from hydrocarbons that are selected for further processing, thereby producing a first heart cut paraffin stream comprising C$_{10}$-C$_{18}$ hydrocarbons;
   hydrotreating a second feed stream comprising waste plastic feedstock comprising C$_{10}$-C$_{18}$ hydrocarbons;
   combining the first heart cut paraffin stream with the second feed stream to form a combined stream;
   hydrotreating the combined stream;
   fractionating the hydrotreated stream to remove paraffins that are heavier and/or lighter than the heart cut range to form a second heart cut paraffin stream;
   dehydrogenating the second heart cut paraffin stream to form a stream comprising olefins;
   purifying the stream comprising the olefins;
   alkylating the stream comprising the olefins with benzene to produce an alkylbenzene; and
   sulfonating the alkylbenzene to form an alkylbenzene sulfonate surfactant.

2. The method according to claim 1, further comprising the step of separating branched and cyclic hydrocarbons from the second heart cut paraffin stream before the step of dehydrogenating to form a linear heart cut paraffin stream, wherein the product olefin is linear.

3. The method according to claim 1, further comprising the step of hydroformylating the olefin to produce an oxo alcohol.

4. The method according to claim 3, further comprising the step of ethoxylating and/or sulfating said oxo alcohol to produce a surfactant.

5. The method according to claim 1, wherein the first heart cut paraffin stream comprises $C_{10}$-$C_{13}$ hydrocarbons.

6. The method according to claim 4, wherein the method includes the step of ethoxylating said oxo alcohol to produce a surfactant.

7. The method according to claim 4, wherein the method includes the step of sulfating said oxo alcohol to produce a surfactant.

8. The method according to claim 4, wherein the method includes the step of ethoxylating and sulfating said oxo alcohol to produce a surfactant.

\* \* \* \* \*